United States Patent
Chen et al.

(10) Patent No.: US 8,349,852 B2
(45) Date of Patent: Jan. 8, 2013

(54) QUINAZOLINONE DERIVATIVES USEFUL AS VANILLOID ANTAGONISTS

(75) Inventors: Weichun Chen, Livingston, NJ (US); Hong-Yong Kim, Whippany, NJ (US); Jessica Liang, Annandale, NJ (US); Michael Mutz, Freiburg (DE); Mahavir Prashad, Montville, NJ (US); Christopher Towler, Quincy, MA (US); Ruoqiu Wu, East Hanover, NJ (US)

(73) Assignee: Novartis AG, Basel (CH)

( * ) Notice: Subject to any disclaimer, the term of this patent is extended or adjusted under 35 U.S.C. 154(b) by 244 days.

(21) Appl. No.: 12/683,317

(22) Filed: Jan. 6, 2010

(65) Prior Publication Data

US 2010/0197705 A1   Aug. 5, 2010

Related U.S. Application Data

(60) Provisional application No. 61/144,250, filed on Jan. 13, 2009.

(51) Int. Cl.
*A61K 31/517* (2006.01)

(52) U.S. Cl. ................................. 514/266.3; 544/290

(58) Field of Classification Search .................. 544/290
See application file for complete search history.

(56) References Cited

FOREIGN PATENT DOCUMENTS

WO    WO 2005/120510    12/2005

OTHER PUBLICATIONS

Jia et al. Role of TRPV receptors in respiratory diseases. 2007. Biochimica et Biophysica Acta, 1772,915-927.*

* cited by examiner

*Primary Examiner* — Brian McDowell
(74) *Attorney, Agent, or Firm* — Michael G. Smith

(57) ABSTRACT

There is described a new polymorphic form of 4-(7-Hydroxy-2-isopropyl-4-oxo-4H-quinazolin-3-yl)-benzonitrile and a method of preparing it.

5 Claims, 1 Drawing Sheet

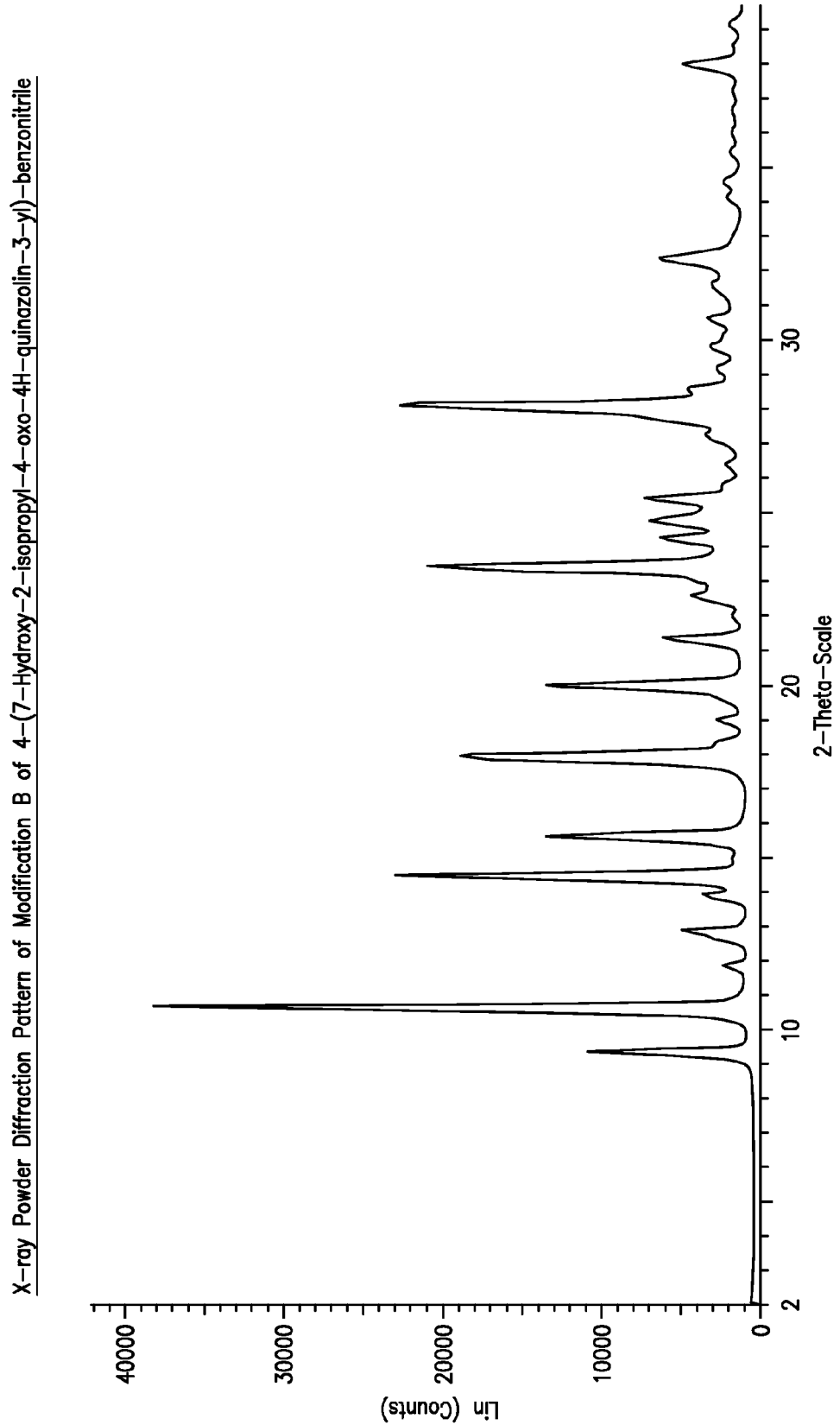

QUINAZOLINONE DERIVATIVES USEFUL AS VANILLOID ANTAGONISTS

CROSS-REFERENCE TO RELATED APPLICATIONS

This application claims benefit of priority to U.S. Provisional Application Ser. No. 61/144,250, filed Jan. 13, 2009.

The present invention relates to a new polymorphic form of a quinazolinone derivative 4-(7-Hydroxy-2-isopropyl 4 oxo-4H-quinazolin-3-yl)-benzonitrile having structural formula I(B) and to a method of preparing it. The invention further relates to a process or method for the manufacture of quinazolinone derivatives useful e.g. as vanilloid antagonists, as well as new intermediates useful in said process or method and processes and methods for their manufacture.

4-(7-Hydroxy-2-isopropyl-4-oxo-4H-quinazolin-3-yl)-benzonitrile having structural formula I(B);

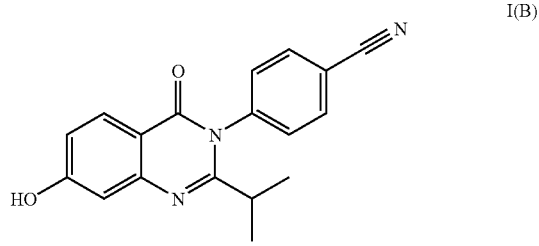 [SMILES: CC(C)c1nc2cc(O)ccc2c(=O)n1-c1ccc(C#N)cc1]

is disclosed in International Patent application No. WO 2005/120510.

In a first aspect the present invention relates to the crystal form B of 4-(7-hydroxy-2-isopropyl-4-oxo-4H-quinazolin-3-yl)-benzonitrile characterized by an X-ray diffraction pattern having three or more peaks at 2θ values selected from 9.3°, 10.6°, 14.4°±0.2°2θ, preferably, 9.3°, 10.6°, 14.4°, 15.5°, 17.9°, 19.9°, 23.4°±0.2°2θ or more preferably, 9.3, 10.6, 12.8, 14.4, 15.5, 17.9, 19.9, 21.3, 23.4, and 28.0±0.2°2θ.

A compound of the invention in crystal form B can be prepared from a solution thereof in a polar organic solvent, such as a mixture of water and a water miscible organic solvent. The water miscible organic solvent may be an alcohol, such as an alkyl C1 to 10 alcohol, preferably a C1 to 6 alcohol and especially ethanol.

When the polar organic solvent comprises a mixture of water and a water miscible organic solvent, the ratio of polar organic solvent, such as a mixture of water and a water miscible organic solvent, the ratio of the water miscible organic solvent and water may vary, depending upon, inter alia, the nature of the water miscible organic solvent and may be in the range of from 1:1 to 1:10, or 1:2 to 1:9, or 1:3 to 1:8 or 1:4 to 1:6 or 1:5.

Therefore, according to a further aspect the invention provides a method of preparing a compound of formula I(B) in crystal form B as hereinbefore defined which comprises crystallising the compound of formula I(B) as hereinbefore defined from a solution thereof in water and a water miscible organic solvent as hereinbefore described.

The crystallisation temperature may be carried out at a temperature of less than 30±3° C. or from 15 to 30±3° C. or from 20 to 30±3° C., e.g. 20±3° C.

Crystal form B may be prepared by crystallising the compound of formula I(B) from a solution thereof in a polar organic solvent as hereinbefore, for example by equilibrating the compound in that solvent over 36 hours at 20±3° C., or analogously such as hereinafter described in Example 1. The crystallisation may be induced by, for example, cooling a supersaturated solution of the compound of formula I in the polar solvent, or by adding to the solution of the compound of formula I a polar solvent in which the compound of formula I is less soluble. The starting solution of the compound of formula I may be at ambient or elevated (up to reflux) temperature.

For the preparation of each of the crystal forms, working up may be carried out generally using known procedures for the separation of the crystallisate from the mother liquor, for example by filtration, with or without the assistance of pressure and/or vacuum, or by centrifugation, and subsequent drying of the crystallisate.

The compound of formula I(B) may be prepared in accordance with the method given in Example 29 of International Patent application WO 2005/120510 or by the process hereinafter described.

Given its vanilloid receptor activity, the compound of formula I(B) in crystal form B is useful in the treatment or prevention of a disease or condition in which vanilloid receptor activation plays a role or is implicated.

Therefore, according to a further aspect of the invention provides the use of a compound of formula I(B) in crystal form B for the preparation of a medicament for the treatment or prevention of a disease or condition in which vanilloid receptor activation plays a role or is implicated.

Specifically, the present invention relates to a process or method for the manufacture of a quinazolinone compound of the formula I

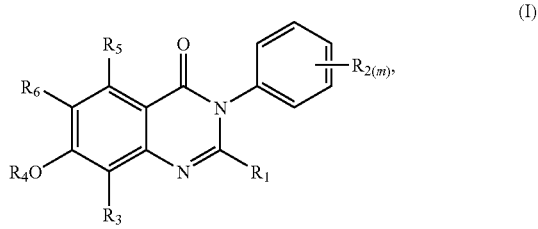

wherein
$R_1$ is $C_1$-$C_6$alkyl, $(C_1$-$C_6$alkyl)$C_1$-$C_6$alkyl, di-$(C_1$-$C_6$alkyl)$C_1$-$C_6$alkyl or $C_3$-$C_6$cycloalkyl, di-(trifluoromethyl)$C_1$-$C_6$alkyl, $R_9$—O—$(C_1$-$C_6$alkyl)- in which the alkyl chain is optionally substitute by trifluoromethyl, (NC)—$C_1$-$C_6$alkyl-, $(R_{10}R_{11}N$—)$C_1$-$C_6$alkyl-, or $(C_1$-$C_6$alkyl)-$SO_2$—$(C_1$-$C_6$alkyl)-, wherein $R_9$, $R_{10}$ and $R_{11}$ are each independently H or $C_1$-$C_6$alkyl;

each $R_2$, independently, is halogen, $C_1$-$C_6$alkyl, halogen-substituted $C_1$-$C_6$alkyl, hydroxy$C_1$-$C_6$alkyl, cyano, a group —C(=O)—$R_{2a}$, where $R_{2a}$ is $C_1$-$C_6$alkyl, $C_1$-$C_6$alkoxy-, $R_{10}R_{11}N$—, $R_{10}R_{11}N$—$(C_1$-$C_6$alkyl)-, —$SO_2$—$(C_1$-$C_6$alkyl), $R_9$—O—(C=O)—, wherein $Rg$, $R_{10}$ and $R_{11}$ are as defined above, unsubstituted or substituted phenyl wherein the substituents are 1 to 4 substituents independently selected from the group consisting of halo, hydroxy and $C_1$-$C_6$-alkyl, or a 5- or 6-membered saturated or unsaturated heterocyclic ring having one, two or three heteroatoms selected from N, O and S and optionally including a further substituent selected from halo;

$R_3$ is hydrogen, halogen, $C_1$-$C_6$alkyl, $C_2$-$C_6$alkenyl, $C_2$-$C_6$alkynyl, hydroxy, hydroxy-substituted $C_1$-$C_6$alkyl, $C_1$-$C_6$alkoxy, $C_3$-$C_6$cycloalkyl, cyano, —C(=O)H, phenyl, $(C_3$-$C_6$cycloalkyl)$C_1$-$C_6$alkoxy, $(C_1$-$C_6$alkoxycarbonylamino)$C_1$-$C_6$alkoxy or $(C_1$-$C_6$alkylcarbonylamino)$C_1$-$C_6$alkoxy;

$R_4$ is H (=hydrogen), or $R_4$—O is esterified hydroxy or etherified hydroxyl; especially $R_4$ is H;

$R_5$ is hydrogen or hydroxy;

$R_6$ is hydrogen, halogen, C1-$C_6$alkyl, $C_2$-$C_6$alkenyl, $C_2$-$C_6$alkynyl, hydroxy, hydroxy-substituted $C_1$-$C_6$alkyl, $C_1$-$C_6$alkoxy, $C_3$-$C_6$cycloalkyl, cyano, —C(=O)H, phenyl, ($C_3$-$C_6$cycloalkyl)$C_1$-$C_6$alkyl, ($C_3$-$C_6$cycloalkyl)$C_1$-$C_6$alkoxy, ($C_1$-$C_6$alkoxycarbonylamino)C1-$C_6$alkoxy or ($C_1$-$C_6$alkylcarbonylamino)$C_1$-$C_6$alkoxy, (amino)$C_1$-$C_6$alkoxy, (dimethylamino)$C_1$-$C_6$alkoxy, or ($C_1$-$C_6$alkoxycarbonyl)$C_1$-$C_6$alkoxy, m is 1 to 5, e.g. 1 or 2, in free form or in salt form.

More preferably, the present invention relates to a method or process for the manufacture of a quinazoline compound of the formula I wherein $R_1$ is $C_1$-$C_6$alkyl, ($C_1$-$C_6$alkyl)$C_1$-$C_6$alkyl, di-($C_1$-$C_6$alkyl)$C_1$-$C_6$alkyl or $C_3$-$C_6$cycloalkyl;

each $R_2$, independently, is halogen, $C_1$-$C_6$alkyl, halogen-substituted $C_1$-$C_6$alkyl, hydroxy$C_1$-$C_6$alkyl, cyano or a group —C(=O)—$R_{2a}$, where $R_{2a}$ is $C_1$-$C_6$alkyl;

$R_3$ is hydrogen, halogen, $C_1$-$C_6$alkyl, $C_2$-$C_8$alkenyl, $C_2$-$C_6$alkynyl, hydroxy, hydroxy-substituted $C_1$-$C_6$alkyl, $C_1$-$C_6$alkoxy, $C_3$-$C_6$cycloalkyl, cyano, —C(=O)H, phenyl, ($C_3$-$C_6$cycloalkyl)$C_1$-$C_6$alkoxy, ($C_1$-$C_6$alkoxycarbonylamino)$C_1$-$C_6$alkoxy or ($C_1$-$C_6$alkylcarbonylamino)$C_1$-$C_6$alkoxy;

$R_4$ is H, or $R_4$—O— is esterified hydroxy or etherified hydroxy;

$R_5$ is hydrogen or hydroxy;

$R_6$ is hydrogen; and m is 1 to 5, e.g. 1 or 2, in free form or in salt form.

Preferred is the method or process for the manufacture of a compound of the formula I wherein $R_1$ is $C_1$-$C_6$alkyl, ($C_1$-$C_6$alkyl)$C_1$-$C_6$alkyl, di-($C_1$-$C_6$alkyl)$C_1$-$C_6$alkyl or $C_3$-$C_6$cycloalkyl;

each $R_2$, independently, is halo, $C_1$-$C_6$alkyl, tri-halo substituted $C_1$-$C_6$alkyl, hydroxy$C_1$-$C_6$alkyl or a group —C(=O)—$R_{2a}$ where $R_{2a}$ is $C_1$-$C_6$alkyl, or especially cyano;

$R_3$ is hydrogen, halo, $C_1$-$C_6$alkyl, hydroxy, $C_1$-$C_6$alkoxy or ($C_3$-$C_6$cycloalkyl)$C_1$-$C_6$alkoxy;

$R_4$ is H, or $R_4$—O— is esterified hydroxyl or etherified hydroxyl; especially $R_4$ is H;

$R_5$ is hydrogen or hydroxy;

$R_6$ is hydrogen; and m is 1 or 2, in free or salt form.

In another particular aspect, the present invention relates to a process or method of manufacture of quinazolinone compounds of the formula Ia

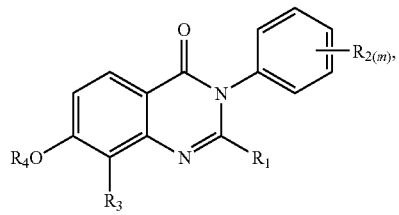

(Ia)

wherein $R_1$ is $C_1$-$C_6$alkyl, ($C_1$-$C_6$alkyl)$C_1$-$C_6$alkyl, di-($C_1$-$C_6$alkyl)$C_1$-$C_6$alkyl or $C_3$-$C_6$cycloalkyl;

each $R_2$, independently, is halogen, $C_1$-$C_6$alkyl, halogen-substituted $C_1$-$C_6$alkyl, hydroxy$C_1$-$C_6$alkyl, cyano or a group —C(=O)—$R_{2a}$, where $R_{2a}$ is $C_1$-$C_6$alkyl;

$R_3$ is hydrogen, halogen, $C_1$-$C_6$alkyl, $C_2$-$C_6$alkenyl, $C_2$-$C_6$alkynyl, hydroxy, hydroxy-substituted $C_1$-$C_6$alkyl, $C_1$-$C_6$alkoxy, $C_3$-$C_6$cycloalkyl, cyano, —C(=O)H, phenyl, ($C_3$-$C_6$cycloalkyl)$C_1$-$C_6$alkoxy, ($C_1$-$C_6$alkoxycarbonylamino)$C_1$-$C_6$alkoxy or ($C_1$-$C_6$alkylcarbonylamino)$C_1$-$C_6$alkoxy;

$R_4$ is H; or $R_4$—O— is esterified hydroxyl or etherified hydroxyl; especially $R_4$ is H; and m is 1 or 2, in free form or in salt form.

Note that formula Ia is a special version of formula I wherein $R_5$ and $R_6$ are hydrogen, respectively.

In a special embodiment of the particular aspect, the present invention relates a process or method for the manufacture to novel quinazolinone compounds of the formula Ia, wherein $R_1$ is $C_1$-$C_6$alkyl, ($C_1$-$C_6$alkyl)$C_1$-$C_6$alkyl, di-($C_1$-$C_6$alkyl)$C_1$-$C_6$alkyl or $C_3$-$C_6$cycloalkyl;

each $R_2$, independently, is halo, $C_1$-$C_6$alkyl, tri-halo substituted $C_1$-$C_6$alkyl, hydroxy$C_1$-$C_6$alkyl or a group

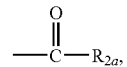

where $R_{2a}$ is $C_1$-$C_6$alkyl; or especially cyano;

$R_3$ is hydrogen, halo, $C_1$-$C_6$alkyl, hydroxy, $C_1$-$C_6$alkoxy or ($C_3$-$C_6$cycloalkyl)$C_1$-$C_6$alkoxy;

$R_4$ is H, or $R_4$—O— is esterified hydroxyl or etherified hydroxyl, especially $R_4$ is H; and m is 1 or 2, especially 1, in free or salt form.

A particularly interesting embodiment of the invention relates to a method or process for the manufacture of a compound of the formula Ia, wherein $R_1$ is ($C_1$-$C_6$alkyl)$C_1$-$C_6$alkyl, especially 1-methylethyl, $R_2$ is halo or especially cyano, $R_3$ is $C_1$-$C_6$-alkyl or especially hydrogen;

$R_4$—O— is esterified hydroxy, such as $R_1$*—C(=O)—O— wherein $R_1$* is as defined below, or in particular $R_4$—O— is hydroxy; and m is 1 or 2, especially 1, in free or salt form.

Most preferred is a compound of the formula Ia wherein $R_1$ is 1-methylethyl;

$R_2$ is cyano in p-position of the phenyl ring relatively to the phenyl carbon binding to the ring nitrogen in formula I;

$R_3$ is hydrogen;

$R_4$ is hydrogen; and m is 1, in free or salt form.

This compound has the chemical designation 4-(7-hydroxy-2-isopropyl-4-oxo-4H-quinazoline-3-yl)-benzonitrile.

BRIEF DESCRIPTION OF THE DRAWINGS

FIG. 1: X-Ray Powder Diffraction Pattern of Modification B of 4-(7-Hydroxy-2-isopropyl-4-oxo-4H-quinazolin-3-yl)-benzonitrile.

DETAILED DESCRIPTION

Terms used in this specification have the following meanings:

"$C_1$-$C_6$alkyl" denotes straight-chain or branched $C_1$ to $C_6$-alkyl, e.g., methyl ethyl, n-propyl, isopropyl, n-butyl, isobutyl, sec-butyl or tert-butyl.

($C_1$-$C_6$alkyl)$C_1$-$C_6$alkyl denotes a $C_1$-$C_6$alkyl that is substituted by a $C_1$-$C_6$alkyl substituent, especially in 1-position, and is in particular 1-methylethyl.

"$C_1$-$C_6$alkoxy" denotes straight-chain or branched $C_1$ to $C_6$-alkyl-oxy, e.g., methoxy, ethoxy, n-propoxy or isopropoxy.

"Halo" denotes halogen which may be I, Br, Cl or F.

"Esterified hydroxy" denotes acyloxy, preferably $C_1$-$C_6$alkanoyloxy, more preferably $C_2$-$C_4$alkanoyloxy, or especially $R_1^*$—C(=O)—O— wherein $R_1^*$ is selected from the group of meanings of $R_1$ defined above or in particular below for a compound of the formula I or Ia, either being not identical or preferably being identical with $R_1$.

"Etherified hydroxy" denotes $C_1$-$C_6$alkoxy, preferably $C_1$-$C_4$alkoxy.

The quinazolinone compounds that are manufactured according to the process of the invention can exist in free or salt form. The invention is to be understood as including the process or methods of manufacture of compounds of formulae (I) and (Ia) in free or salt form. In the latter connection, an example which is of interest are suitable pharmaceutically acceptable acid addition salts for pharmaceutical use in accordance with the invention which include, in particular, the hydrochloride salt. The free form is obtainable according to one further particular embodiment of the invention.

In formulae (I) and (Ia), the following significances are preferred independently, collectively or in any combination or sub-combination:

(a) $R_1$ is $C_1$-$C_4$alkyl, ($C_1$-$C_6$alkyl)$C_1$-$C_6$alkyl, di-($C_1$-$C_6$alkyl)$C_1$-$C_6$alkyl or cyclopropyl, especially ($C_1$-$C_4$alkyl)$C_1$-$C_4$alkyl;

(b) each $R_2$, independently, is chloro, fluoro, $C_1$-$C_4$alkyl, trifluoro-substituted $C_1$-$C_4$alkyl, more preferably trifluoromethyl, $C_1$-$C_4$alkylcarbonyl, more preferably methylcarbonyl, or hydroxy$C_1$-$C_4$alkyl, more preferably hydroxymethyl;

(c) $R_3$ is hydrogen (preferred), or further chloro, bromo, $C_1$-$C_4$alkyl, hydroxy, $C_1$-$C_4$alkoxy or ($C_3$-$C_6$cycloalkyl)$C_1$-$C_4$alkoxy;

(d) $R_4$ is H.

There are known processes for the manufacture of such compounds, e.g. as disclosed in WO 2005/120510 A1. There a process is disclosed for obtaining a compound of the formula I or Ia wherein $R_4$ is hydroxyl. This scheme involves a Sandmeyer reaction of the 7-amino substituted quinazolin-4-one compound of formula 3 which has been prepared before as set forth in Scheme A in said application, with concentrated sulphuric acid and sodium nitrite to obtain the 7-hydroxy substituted quinazolin-4-one compound of formula 4. However, this approach requires the circumstantial detour via an amino precursor that needs to be synthesized first according to another process (A) disclosed in WO 2005/120510 A1 and in addition requires the rather harsh Sandmeyer reaction conditions.

Other ways of synthesis may imply the presence of a protected hydroxy group corresponding to $R_4$ which is then deprotected—this, however, requires the last synthesis step is a deprotection which may lead to the requirement of further purification steps, especially if deprotection is not complete or leads to side reactions. This way of synthesis is e.g. exemplified in WO 2007/065662 A2 where e.g. a triisopropylsilyl-protecting group is used.

Surprisingly, now a process or method has been found that allows for the synthesis of the compounds of the formula I and Ia, or salts thereof, without the requirement of going via an amino compound and without the requirement to remove a protecting group from $R_4$ in the last step.

Both WO2007/065662 A2 and WO 2005/120510 A1 are preferably incorporated here by reference regarding their disclosure of compounds falling under formula I, especially in their Examples, to support the scope of compounds accessible with the present process or method of manufacture.

(A) The new method or process comprises reacting a compound of the formula II,

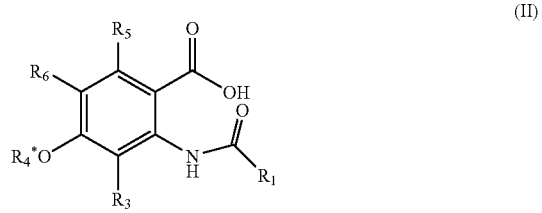

(II)

wherein $R_4^*$ is $R_1^*$—C(=O)— wherein $R_1^*$ is as defined for a compound of the formula I or preferably Ia, or $R_4^*$ preferably is H, and $R_1$ and $R_3$, $R_5$ and $R_6$ are as defined for a compound of the formula I, preferably $R_5$ and $R_6$ are hydrogen and $R_1$, $R_3$ and $R_4$ are as defined for a compound of the formula Ia, and/or preferably $R_1$ is ($C_1$-$C_6$alkyl)$C_1$-$C_6$-alkyl, such a 1-methylethyl, or a salt thereof, under condensation and cyclisation conditions with an aniline compound of the formula III,

(III)

wherein $R_2$ and m are as defined above for a compound of the formula I or preferably of a compound of the formula II, to give a corresponding compound of the formula I or preferably Ia wherein $R_4$ is $R_1^*$—C(=O)— with $R_1^*$ as defined for a compound of the formula I or preferably Ia, or preferably $R_4$ is H, and the remaining substituents are as defined for formula I or preferably Ia, respectively;

and, if desired, acylating or etherifying the free hydroxyl group $R_4$ with a compound of the formula (IV)

$R_4''$—X    (IV)

wherein X is OH or an active derivative thereof (such as halo, e.g. chloro or bromo, or arylsulfonyloxy, e.g. toluolsulfonyloxy) and $R_4''$ is the an esterifying acid or an etherifying moiety (especially acyl, preferably $C_1$-$C_6$alkanoyl, more preferably $C_2$-$C_4$alkanoyl, or especially $R_1^*$—C(=O) wherein $R_1^*$ has the same meaning as $R_1$ defined above or below for a compound of the formula I or Ia; or $C_1$-$C_6$alkoxy, preferably $C_1$-$C_4$alkoxy) completing esterified or etherified hydroxyl $R_4$—O as defined for a compound of the formula I or preferably Ia;

and/or, if desired, converting a resulting free compound of the formula I or preferably Ia into its salt or converting a resulting salt or a compound of the formula I or preferably Ia into its free form.

The condensation and cyclisation conditions can be such that either a two step reaction takes place via an intermediate of the formula V resulting from condensation,

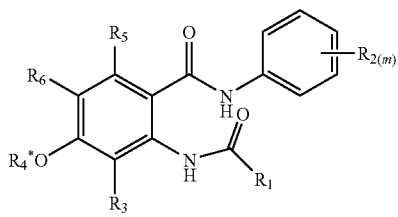

wherein the symbols $R_1$, $R_2$, m, $R_3$, $R_4^*$, $R_5$ and $R_6$ have the meanings indicated for compounds of the formula II and III, respectively, followed by cyclisation (sequential version with optional isolation of the intermediate of the formula V or further processing thereof in the next step without complete isolation); then in the first reaction acylation of the amino compound (condensation) can take place, e.g. by activating the carboxylic group in formula II e.g. with an acid anhydride or halogenide, such as an organic carboxylic acid halogenide, e.g. oxalyl chloride, in an appropriate solvent to the corresponding mixed anhydride or halogenide, e.g. chloride, in an appropriate solvent, e.g. a halo-organic solvent, such as methylene chloride or chloroform, or a di-alkylated carboxylic acid amide, such as dimethyl formamide, or mixtures of two or more such solvents, at appropriate temperatures, e.g. 0 to 50° C., if useful in the presence of a tertiary nitrogen base, such as triethylamine, or by using a coupling reagent customary in peptide synthesis under appropriate conditions, if desired followed by purification or isolation of the intermediate of the formula V; and in the second reaction cyclisation can be made under dehydrating conditions, e.g. by adding an inorganic acid halogenide, such as phosphorous trichloride or sulfurylchloride in an appropriate solvent, e.g. an aromatic solvent, such as toluene or xylene, or concentrated sulfuric acid to the intermediate, preferably at temperatures in the range from 0 to 120° C.; or much preferably, however, using a one pot synthesis with parallel ("simultaneous") condensation and cyclisation of the starting materials of the formula II and Ill in the presence of an appropriate condensation and dehydration agent, especially an acid halogenide, especially an inorganic acid halogenide, such as sulfurylchloride, sulfuryibromide, sulfuryliodide, phosphoryl chloride (phosphorous oxychloride), phosphoryl bromide, phosphoryl iodide or preferably phosphorous tribromide, phosphorous triiodide or especially phosphorus trichloride, in an appropriate solvent, such as an aromatic solvent, e.g. toluene or xylene, or a nitrile, e.g. acetonitrile, or mixtures of two or more such solvents, with temperatures e.g. in the elevated range, such as between 30 and 120° C., such as 50 to 100° C.

Optional conversions: If desired, a compound of the formula I that results thus wherein $R_4$ is hydrogen (the preferred reaction leads to this product, employing a compound of the formula II wherein $R_4^*$ is hydrogen) can then be converted to the corresponding compound wherein $R_4$—O— is etherified or esterified hydroxyl, especially as defined above, by esterification with a corresponding acid, such as a carboxylic acid, especially a $C_1$-$C_6$-alkanoic acid or an acid of the formula $R_1^*$—C(=O)—OH with $R_1^*$ as defined for a compound of the formula Ia, or especially or an active derivative (carboxyl-activated form) thereof, e.g. an acid anhydride, an acid halogenide or an activated ester, e.g. in an appropriate solvent, such as an ether, e.g. dioxane, e.g. in the presence of a tertiary amine, such as triethylamine, e.g. at temperatures in the range from 0 to 50° C., or for etherifying by forming an ether, especially a $C_1$-$C_6$-alkoxy ether, preferably $C_1$-$C_4$alkoxy, e.g. by reaction of the corresponding (e.g. $C_1$-$C_6$-alkyl, especially $C_1$-$C_4$alkyl)halogenide, e.g. chloride or iodide, e.g. under Williamson synthesis conditions (presence of a base, e.g. an alkali metal hydride or an alkali metal carbonate, such as sodium or potassium carbonate).

However, the reaction of the compound of the formula II wherein $R_4^*$ is H is preferred as it leads directly to the hydroxyl $R_4$ compound of formula I, avoiding a cleavage reaction to remove an OH protecting group as known from WO 2007/065662 that leads to mixtures of protected and de-protected product and thus not requiring a further purification step. This synthesis method is therefore particularly preferred for compounds of the formula I, preferably Ia, especially for 4-(7-hydroxy-2-iospropyl-4-oxo-4H-quinazoline-3-yl)-benzonitrile, wherein $R_4$—O— is hydroxy.

Further, if desired, a resulting salt of a compound of the formula I can be converted into the free form or a free form of a compound of the formula I can be converted into the salt form, especially into a pharmaceutically acceptable salt, e.g. the hydrochloride acid addition salt, according to standard methods, e.g. using ion exchangers or the addition of acids (to form acid addition salts) or bases (e.g. followed by isolation of the resulting salt). For example, acid addition salts with organic (e.g. carboxylic or sulfonic acids, such as acetic acid or methanesulfonic acid) or inorganic acids (such as hydrohalic acids, e.g. HCl) are possible.

If desired, a compound of the formula I obtained directly or via its salt or a salt of a compound of the formula I can then be re-crystallized e.g. from a first polar organic solvent, such as an alcohol, e.g. ethanol, adding a second more polar solvent, e.g. water, in an (on a volume by volume basis) lower amount than the first solvent, or according to any other customary method known or readily derivable for a skilled person.

($B^i$) The compound of formula II wherein $R_4^*$ is $R_1^*$—C(=O)— wherein $R_1^*$ is as defined for a compound of the formula I or preferably Ia, especially being ($C_1$-$C_6$-alkyl)$C_1$-$C_6$-alkyl, in particular 1-methylethyl, or $R_4^*$ preferably is H, and the other moieties are as defined for a compound of the formula II above, can preferably be obtained by oxidizing (at its methyl group which is oxidized to a carboxyl group) and (see under ($B^{ii}$) below), if $R_4^*$ is $R_1^*$—C(=O)— as just defined and thus not hydrogen (with $R_1^*$ preferably being identical to $R_4^*$), then if desired (and preferably obligatorily) in addition (in a subsequent process step to give the corresponding compound of the formula II wherein R4* is hydrogen) hydrolyzing a compound of the formula VI,

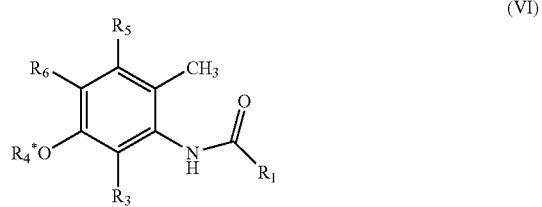

wherein the moieties are as defined for a compound of the formula I or Ia, and R4* is R$_1$*—C(=O)—, wherein R$_1$* is as defined for a compound of the formula I or preferably Ia, especially being (C$_1$-C$_6$-alkyl)C$_1$-C$_6$-alkyl, such as (C$_1$-C$_4$-alkyl)C$_1$-C$_4$-alkyl, in particular 1-methylethyl, preferably wherein R$_4$* and R$_1$—C(=O) are identical, to the corresponding compound of the formula II wherein R$_4$* is H (which can be obtained by oxidation followed by hydrolysis from a compound of the formula VI wherein R$_4$* is R$_1$*—C(=O)— as just defined or without hydrolysis wherein R$_4$* is H) or R$_4$* (which can be obtained by oxidation (without hydrolysis) from a compound of the formula VI wherein R$_4$* is R$_1$*—C(=O)— as just defined).

The oxidizing step preferably takes place with an oxidant, such as a dichromate, such as sodium dichromate, chromium trioxide, nitric acid, a metal hypochlorite, such as LiOCl, NaOCl, KOCl or Ca(OCl)$_2$ in the presence of heavy metal salts (see e.g. EP 0 897 910) or oxygen in the presence of a catalyst, such as cobalt or manganese naphthenates, or preferably using a permanganate as oxidant, especially potassium permanganate, in an appropriate solvent, such as water, preferably in the presence of an alcohol, such as butanol, e.g. tert-butanol, e.g. at temperatures in the range from 0° C. to the reflux temperature of the reaction mixture, for example from 5 to 40° C., such as from 15 to 30° C. (If an excess of oxidant is used, this can then be neutralized by reaction with a further reductant, such as sodium- or potassium-hydrogensulfite).

(B$^{ii}$) The resulting compound after oxidation of a compound of the formula VI wherein R$_4$* is R$_1$*—C(=O)— is a compound of the formula II which can then, in an additional step, advantageously and thus preferably (as mentioned) be hydrolyzed (removing the R$_1$*—C(=O)—) to yield the corresponding compound wherein R$_4$* is H (hydrogen). The advantage is especially so bee seen in that then the corresponding compound of the formula II can directly be subjected to the cyclisation to the corresponding compound of the formula I or Ia wherein R$_4$ is H without the need of cleaving off a protecting group from the hydroxyl at the final stage, thus allowing to obtain especially pure compound of the formula I without protected derivative as impurity, thus making purification at the last stage much simpler than in the prior art. The hydrolysis can take place under customary conditions for the cleavage of carboxylic acid esters, e.g. with acids or preferably bases, such as soluble metal hydroxides, e.g. alkaline metal hydroxides, such as potassium hydroxide or especially sodium hydroxide, in an appropriate solvent, e.g. an aqueous solvent, such as water, or preferably an ether, especially a cyclic (preferably water soluble) ether, such as tetrahydrofuran or dioxane, or especially a mixture thereof with water, e.g. at temperatures in the range from 0 to 50° C., e.g. from 15 to 25° C. This results in a compound of the formula II wherein R$_4$* is H.

The compound of the formula II can be obtained and used in the synthesis of the formula I or Ia in free or in salt form, as desired or useful.

(C) A compound of the formula VI (wherein especially R$_4$* is R$_1$*—C(=O)— and wherein R$_1$* is as defined for a compound of the formula I or Ia, especially being (C$_1$-C$_6$-alkyl)C$_1$-C$_6$-alkyl, in particular 1-methylethyl) can be synthesized preferably by acylating a compound of the formula VII,

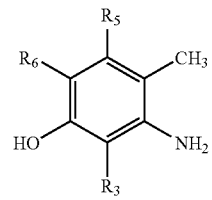
(VII)

(said expression including the free compound or a salt thereof) wherein R$_3$, R$_5$ and R$_6$ are as defined above or below for a compound of the formula I, especially Ia, with an acid of the formula VIII,

R$_1$"—COOH  (VIII)

or preferably a reactive derivative thereof, either simultaneously reacting the free OH and NH$_2$ group in formula VII (which is preferred in view of its striking process economy) or reacting these groups sequentially, then either using the same acid of formula VIII or its reactive derivative, or two different acids of the formula VIII, in the latter case the first to acylate the first (usually the NH$_2$ group), the second to acylate the second group (usually the OH group).

Most preferred are the preceding processes wherein R$_1$* and R$_1$ are identical in all compounds where these symbols are mentioned, which allows to synthesize the compounds of the formula VII wherein R$_1$ and R$_1$* are identical in one step using a compound of the formula VIII wherein R$_1$" is identical to R$_1$ and R$_1$*, preferably using sufficient acid of the formula VIII to introduce R$_1$—C(=O)— and R$_1$*—C(=O)— in parallel (simultaneously) at the OH and the NH$_2$ group acylated in one common step. Most preferably each of R$_1$* and R$_1$ and thus R'$_1$' in the compound of the formula VIII is (C$_1$-C$_6$alkyl)C$_1$-C$_6$alkyl, more preferably (C$_1$-C$_4$alkyl)C$_1$-C$_4$alkyl, most preferably 1-methylethyl.

A preferred embodiment of the invention relates to a sequence of the reactions given under (B$^i$), followed by (B$^{ii}$) and then (A) given above, especially wherein R$_1$* and R$_1$ each are identical (C$_1$-C$_6$alkyl)C$_1$-C$_6$alkyl, more preferably (C$_1$-C$_4$alkyl)C$_1$-C$_4$alkyl, most preferably 1-methylethyl, especially where the reaction of the compound of the formula VI is under oxidation of the methyl group to carboxyl and hydrolysis of R$_4$*—O with R$_4$*=R$_1$*—C(=O)— to hydroxyl (with R$_4$*=H) and without subsequent esterification or etherification to yield hydrogen as R$_4$ in the obtainable compound of formula I.

Another particularly preferred embodiment of the invention relates to a sequence of the reactions given under (C), followed by (B$^i$) and then (B$^{ii}$) and finally (A) above, especially wherein R$_1$* and R$_1$ each are identical (C$_1$-C$_6$alkyl)C$_1$-C$_6$alkyl, more preferably (C$_1$-C$_4$alkyl)C$_1$-C$_4$alkyl, most preferably 1-methylethyl, especially where the reaction of the compound of the formula VI is under oxidation of the methyl group to carboxyl and hydrolysis of R$_4$*—O with R$_4$*=R$_1$*—C(=O)— to hydroxyl (with R$_4$*=H) without subsequent esterification or etherification to yield hydrogen as R$_4$ in the obtainable compound of formula I.

Reactive derivatives of acids (especially carboxylic acids) or carboxyl-activated forms of carboxylic acids (e.g. of the formula II) mentioned above or below are especially the corresponding acid anhydrides, e.g. the symmetrical anhydride or mixed anhydride with another carboxylic or a sulfonic acid, such as acetic acid or propionic acid, the corresponding acid halides, e.g. acids chlorides or bromides, the corresponding active esters, e.g. the o-, m- or especially p-nitrophenyl ester, the 2,4-dinitrophenyl ester, the pentafluorophenyl ester or the N-hydroxysuccinimide ester, which can be used as such or formed in situ in the reaction mixtures, e.g. in the presence of a coupling reagent customary in peptide synthesis. Preferred are the acid halides, especially the acid chlorides.

A coupling agent useful in peptide synthesis is, for example, dicyclohexylcarbodiimide/1-hydroxybenzotriazole (DCC/HOBT); bis(2-oxo-3-oxazolidinyl)phosphinic chloride (BOPCl); O-(1,2-dihydro-2-oxo-1-pyridyl)-N,N,N',N'-tetramethyluronium tetrafluoroborate (TPTU); O-benzotriazol-1-yl)-N,N,N',N'-tetramethyluronium tetrafluoroborate (TBTU); (benzotriazol-1-yloxy)-tripyrrolidinophosphonium-hexafluorophosphate (PyBOP), O-(1H-6-chlorobenzotriazole-1-yl)-1,1,3,3-tetramethyluronium hexafluorophosphate, 1-(3-dimethylaminopropyl)-3-ethylcarbodiimide hydrochloride/hydroxybenzotriazole or/1-hydroxy-7-azabenzotriazole (EDC/HOBT or EDC/HOAt) or HOAt alone, or with (1-chloro-2-methyl-propenyl)-dimethylamine. For review of some other possible coupling agents, see e.g. Klauser; Bodansky, *Synthesis* (1972), 453-463. The reaction mixture is, for example, stirred at a temperature of between approximately –20 and 50° C., especially between 0° C. and 30° C., e.g. at room temperature, and the reaction usually takes place in a suitable solvent, for example a halogenated hydrocarbon, such as methylene chloride, N,N-dimethylformamide, N,N-dimethylacetamide, N-methyl-2-pyrrolidone, 4-(N,N-dimethylamino)-pyridine or acetonitrile, or a mixture of two or more such solvents, and usually with addition of a suitable base, for example triethylamine, diisopropylethylamine (DIPEA) or N-methylmorpholine.

Compounds of the formula VIII (and also their active derivatives) are known, can be prepared according to methods known in the art or they are commercially available.

Compounds of the formula VII, or salts thereof, are also commercially available, can be prepared according to methods known in the art or are otherwise known, especially the compound wherein $R_3$, $R_5$ and $R_6$ each are hydrogen; or a salt thereof. For example, they can be obtained from AK Scientific, Inc (897-4G Independence Ave. Mountain View, Calif., 94043, USA.

For example, a compound of the formula VII can be obtained by deprotection of its hydroxyl protected precursor (e.g. described in WO 2007/065662) by deprotection of the hydroxyl group (e.g. if it is a TIPS protecting group (triisopropylsilanyl)) according to methods known in the art, or it is commercially available.

Another embodiment of the invention relates to a compound of the formula V wherein $R_1$, $R_2$, $R_3$, $R_4^*$, $R_5$, $R_6$ and m are as defined above or below for a compound of the formula I or preferably Ia, where preferably $R_4^*$ is H and $R_1$ is ($C_1$-$C_6$-alkyl)$C_1$-$C_6$-alkyl, such as ($C_1$-$C_4$-alkyl)$C_1$-$C_4$-alkyl, in particular 1-methylethyl and the other moieties are as defined above or below for a compound of the formula I (especially Ia).

A further embodiment of the invention relates to a novel compound of the formula VI wherein the moieties are as defined for a compound of the formula I or Ia, and $R_4^*$ is $R_1^*$—C(=O)—, wherein $R_1^*$ is as defined for a compound of the formula I or preferably Ia, especially being ($C_1$-$C_6$-alkyl)$C_1$-$C_6$-alkyl, such as ($C_1$-$C_4$-alkyl)$C_1$-$C_4$-alkyl, in particular 1-methylethyl, so that most preferably $R_1^*$ and $R_1$ are identical.

Another embodiment of the invention relates to a novel compound of the formula II wherein $R_4^*$ is $R_1^*$—C(=O)— wherein $R_1^*$ is as defined for a compound of the formula I or preferably Ia, or preferably $R_4^*$ is hydrogen, and the other moieties are as defined above for a compound of the formula I or Ia, preferably a compound of the formula II wherein $R_4^*$ is $R_1^*$—C(=O)— and each of $R_1^*$ and $R_1$ is identical and is preferably ($C_1$-$C_6$alkyl)$C_1$-$C_6$-alkyl, such as ($C_1$-$C_4$-alkyl)$C_1$-$C_4$-alkyl, in particular 1-methylethyl, or wherein $R_4^*$ is hydrogen and $R_1$ is as defined for a compound of the formula I, especially as ($C_1$-$C_6$-alkyl)$C_1$-$C_6$-alkyl, such as ($C_1$-$C_4$-alkyl)$C_1$-$C_4$-alkyl, in particular 1-methylethyl; or a salt thereof; or a salt or a carboxyl-activated from thereof.

Yet a further embodiment of the invention relates to a novel compound of the formula II wherein $R_4^*$ is hydrogen and the other moieties are as defined above for a compound of the formula I or especially Ia, preferably wherein $R_1$ is ($C_1$-$C_6$-alkyl)$C_1$-$C_6$-alkyl, such as ($C_1$-$C_4$-alkyl)$C_1$-$C_4$-alkyl, in particular 1-methylethyl, or a salt or a carboxyl-activated form thereof.

The invention also relates to a method or process for the manufacture of the novel compounds of the formulae V, VI or II, including one or in particular more or especially all of the process steps used above or below in their synthesis.

The present invention also relates to the embodiments described in the claims, especially the dependent claims, in their originally disclosed version which are incorporated into the present description by reference.

Where the term "solvent" or "solvents" is used herein, this includes single solvents and solvent mixtures.

Working up the reaction mixtures according to the above processes and purification of the compounds thus obtained may be carried out in accordance with known procedures.

Salts, e.g. acid addition salts may be produced from the free bases or e.g. in the case of a compound of the formula II with the carboxyl group from the free acids in known manner, and vice-versa. For example, salts of the carboxyl compounds of the formula II may be obtained with corresponding cation salts, such as quaternary or tertiary ammonium salts or metal salts, e.g. alkaline or earth alkaline metal salts, such as sodium, potassium, lithium, calcium or magnesium salts.

Compounds of formulae (I) and (Ia) in optically pure form can be obtained from the corresponding racemates according to well-known procedures, e.g., HPLC with chiral matrix. Alternatively, optically pure starting materials can be used.

Stereoisomeric mixtures, e.g., mixtures of diastereomers, can be separated into their corresponding isomers in a manner known per se by means of suitable separation methods. Diastereomeric mixtures, e.g., may be separated into their individual diastereomers by means of fractionated crystallisation, chromatography, solvent distribution and similar procedures. This separation may take place either at the level of a starting compound or in a compound of formula (I) or (Ia) itself. Enantiomers may be separated through the formation of diastereomeric salts, e.g., by salt formation with an enantiomer-pure chiral acid, or by means of chromatography, e.g., by HPLC, using chromatographic substrates with chiral ligands.

In any additional process steps, carried out as desired, functional groups of the starting compounds which should not take part in the reaction may be present in unprotected form or may be protected, e.g., by one or more of the protecting groups mentioned below. The protecting groups are then wholly- or partly-removed according to one of the methods described there. Preferably no further protection than indicated in the process descriptions given above or in the claims is necessary.

Such protecting groups may already be present in precursors and should protect the functional groups concerned against unwanted secondary reactions. It is a characteristic of protecting groups that they lend themselves readily, i.e., without undesired secondary reactions, to removal, typically by solvolysis, reduction, photolysis or also by enzyme activity, e.g., under conditions analogous to physiological conditions, and that they are not present in the end-products. The skilled artisan knows, or can easily establish, which protecting groups are suitable with the reactions mentioned hereinabove and hereinafter.

The protection of such functional groups by protecting groups, the protecting groups themselves, and their removal reactions are described, e.g., in standard reference works, such as J. F. W. McOmie, *Protective Groups in Organic Chemistry*, Plenum Press, London and NY (1973); T. W. Greene, *Protective Groups in Organic Synthesis*, Wiley, N.Y. (1981); *The Peptides*; Volume 3, E. Gross and J. Meienhofer, Eds., Academic Press, London and NY (1981); *Methoden der organischen Chemie (Methods of organic chemistry)*, Houben Weyl, 4$^{th}$ Edition, Volume 15/1, Georg Thieme Verlag, Stuttgart (1974); H. D. Jakubke and H. Jescheit, *Aminosauren, Peptide, Proteine (Amino acids, peptides, proteins)*, Verlag Chemie, Weinheim, Deerfield Beach, and Basel (1982); and Jochen Lehmann, *Chemie der Kohlenhydrate: Monosaccharide und Derivate (Chemistry of carbohydrates: monosaccharides and derivatives)*, Georg Thieme Verlag., Stuttgart (1974).

Preferably, no further protecting groups are used in order to simplify the synthesis, especially according to the preferred synthesis processes or methods described above and below.

All process steps described herein can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralizing agents, e.g., ion exchangers, typically cation exchangers, e.g., in the H$^+$ form, depending on the type of reaction and/or reactants at reduced, normal or elevated temperature, e.g., in the range from −100° C. to about 190° C., preferably from about −80° C. to about 150° C., e.g., at −80° C. to 60° C., at room temperature, at −20° C. to 40° C. or at the boiling point of the solvent used, under atmospheric pressure or in a closed vessel, where appropriate under pressure, and/or in an inert atmosphere, e.g., under argon or nitrogen.

The compounds of formulae (I) and (Ia) and I(B) in crystal form B, and their pharmaceutically acceptable salts and, where possible, pharmaceutically acceptable acid addition salts, have beneficial pharmacological activity and, therefore, are useful as pharmaceuticals. In particular, the compounds of formulae (I) and (Ia) exhibit human vanilloid antagonistic activity, see e.g. WO 2007/065662 A2 and WO 2005/120510 A1. More particularly, the compounds of formulae (I) and (Ia) are active at the TRPVI receptor as demonstrated by their ability to inhibit capsaicin and low pH activation of the TRPVI ion channel.

The compounds of formulae (I) and (Ia) and I(B) in crystal form B, e.g., the compounds of the examples, show TRPVI receptor antagonist activity having IC$_{50}$ values in the range 0.004-30 μM.

According to a further aspect the invention provides a method of treatment or alleviation of a disease or condition in which vanilloid receptor activation plays a role or is implicated which comprises administering to a mammal a therapeutically effective amount of a compound of formula I(B) in crystal form B, For example, the compound of Example 1 shows potent inhibition of low pH-, capsaicin-, anandamide- and NADA-stimulation of human TRPV1 with IC$_{50}$ values of 5, 12, 10 and 27 nM, respectively. The antagonist activity at human TRPV1 is non-competitive and reversible.

In view of the above, the compounds of formulae (I) and (Ia) and I(B) in crystal form B, are useful as vanilloid receptor blockers, e.g., in the treatment of diseases and conditions in which vanilloid receptor activation plays a role or is implicated. Such conditions include, in particular, pain, e.g., bone and joint pain (osteoarthritis), cancer pain, myofascial pain (muscular injury, fibromyalgia) and perioperative pain (general surgery, gynecologic surgery).

The compounds of formulae (I) and (Ia) and I(B) in crystal form B, are particularly useful In the treatment or prevention of chronic pain or acute pain, especially inflammatory, e.g., chronic inflammatory pain; inflammatory diseases, e.g., inflammatory airways disease, e.g., chronic obstructive pulmonary disease (COPD), or in asthma; cough; urinary incontinence; migraine; visceral disorders, e.g., inflammatory bowel disease; rhinitis; cystitis, e.g. interstitial cystitis; pancreatitis; uveitis; inflammatory skin disorders; and rheumatoid arthritis.

The compounds of formulae (I) and (Ia) and I(B) in crystal form B, are thus useful as vanilloid receptor antagonists, e.g., for the treatment of pain of various genesis or aetiology and as anti-inflammatory and/or anti-edemic agents for the treatment of inflammatory reactions, diseases or conditions, as well as for the treatment of allergic responses. Having regard to their analgesic/anti-inflammatory profile, they are useful for the treatment of inflammatory pain, for the treatment of hyperalgesia and, in particular, for the treatment of severe chronic pain. They are, e.g., useful for the treatment of pain, inflammation and/or oedema consequential to trauma, e.g., associated with burns, sprains, fractures or the like, subsequent to surgical intervention, e.g., as post-operative analgesics, as well as for the treatment of inflammatory pain of diverse genesis, e.g., for the treatment of osteo and rheumatoid arthritis and rheumatic disease, teno-synovitis and gout. They are further suitable as analgesics for the treatment of pain associated with, e.g., angina, menstruation or cancer. As anti-inflammatory/anti-oedema agents, they are further useful, e.g., for the treatment of inflammatory skin disorders, e.g., psoriasis and eczema.

As vanilloid receptor blockers, the compounds of formula (I) and (Ia) and I(B) in crystal form B, are also useful as smooth muscle relaxants, e.g., for the treatment of spasm of the gastrointestinal tract or uterus, e.g., in the therapy of Crohn's disease, ulcerative colitis or pancreatitis.

The compounds of formula (I) and (Ia) and I(B) in crystal form B, are in particular useful as agents for the therapy of airways hyperreactivity and for the treatment of inflammatory events associated with airways disease, in particular, asthma. In addition, the agents of invention may, e.g., be used for the control, restriction or reversal of airways hyperreactivity in asthma.

Inflammatory or obstructive airways diseases to which the present invention is applicable include asthma of whatever type or genesis including both intrinsic and, especially, extrinsic asthma. Thus, the compounds of formula (I) and (Ia) and I(B) in crystal form B, are useful for the treatment of allergic asthma, as well as, e.g., exercise induced asthma, occupational asthma, asthma induced following bacterial infection, other non-allergic asthmas and "wheezy-infant syndrome".

Efficacy in the treatment of asthma will be evidenced by reduced frequency or severity of symptomatic attack, e.g., of acute asthmatic or bronchoconstrictor attack and by reduced requirement for other, symptomatic therapy, e.g., anti-inflammatory, e.g., corticosteroid; or bronchodilator, e.g., β2 adrenergic, therapy.

Inflammatory or obstructive airways diseases to which the present invention is applicable further include pneumoconiosis (an inflammatory, commonly occupational, disease of the lungs, frequently accompanied by repeated inhalation of dusts) of whatever type or genesis including, e.g., aluminosis, anthracosis, asbestosis, chalicosis, ptilosis, siderosis, silicosis, tabacosis and, in particular, byssinosis.

Further inflammatory or obstructive airways diseases and conditions for which the compounds of formulae (I) and (Ia) and I(B) in crystal form B, may be used include adult respiratory distress syndrome (ARDS), chronic obstructive pulmonary or airways disease (COPD or COAD), and bronchitis. The compounds of formulae (I) and (Ia) and I(B) in crystal form B, may also be used for the treatment of allergic and vasomotor rhinitis.

In addition to the foregoing, the compounds of formulae (I) and (Ia) and I(B) in crystal form B, are also indicated for use in the therapy of septic shock, e.g., as anti-hypovolaemic and/or anti-hypotensive agents; in the treatment of inflammatory bowel disease; cerebral oedema; headache; migraine; inflammatory skin disease, such as eczema and psoriasis; inflammatory disorders of the gut, e.g., irritable bowel syndrome; Crohn's disease; ulcerative colitis; and cystitis, e.g., interstitial cystitis, nephritis and uveitis.

The agents of the invention are useful in the prevention and treatment of diseases and conditions in which human VR1 activation plays a role or is implicated, and therefore susceptible to treatment by the modulation (preferably antagonism) of VR1 receptors. Such conditions include chronic pain with an inflammatory component such as rheumatoid arthritis; bone and joint pain (osteoarthritis); post-surgical pain; musculo-skeletal pain such as fibromyalgia; myofascial pain syndromes; headache, including migraine, acute or chronic tension headache, cluster headache, temporomandibular pain, and maxillary sinus pain; ear pain; episiotomy pain; burns, and especially primary hyperalgesia associated therewith; deep and visceral pain, such as heart pain, muscle pain, eye pain, orofacial pain, abdominal pain, gynaecological pain, such as dysmenorrhoea, and labour pain; pain associated with the urogenital tract such as cystitis and vulvadynia; inflammatory skin disorders, for example psoriasis and eczema, or itch of non-specific origin; chronic pain associated with nerve injury and/or diseases affecting the nervous system, such as neuropathic pain associated with post-herpetic neuralgia, diabetic neuropathy, chemotherapy-induced neuropathy, amputations ("phantom limb pain"), nerve entrapment and brachial plexus avulsions, low back pain, sciatica and ankylosing spondylitis, reflex sympathetic dystrophy and other chronic nerve injuries; complex regional pain syndromes; central nervous system pain, such as pain due to spinal cord or brain stem damage, or stroke; gout; scar pain; pain associated with carcinoma, often referred to as cancer pain; respiratory diseases including asthma, aluminosis, anthracosis, inflammatory airways disease, e.g. Chronic Obstructive Pulmonary Disease; chronic bronchitis, asbestosis, chalicosis, ptilosis, siderosis, silicosis, tabacosis, byssinosis; rhinitis including allergic rhinitis such as seasonal and perennial rhinitis, and non-allergic rhinitis; cough, either idiopathic or associated with respiratory diseases such as COPD, asthma, cystic fibrosis, cancer, or gastrointestinal disturbances such as gastro-oesophageal reflux; autoimmune diseases; gastrointestinal disorders including but not restricted to irritable bowel syndrome, Crohn's disease, ulcerative colitis, pancreatitis, inflammatory bowel disease. Diseases of the urogenital tract, particularly cystitis; urinary incontinence including bladder detrusor hyper-reflexia and bladder hypersensitivity.

According to a further aspect the invention provides the use of a compound formula I(B) in crystal form B, for the preparation of a medicament for the treatment or prevention of chronic or acute pain.

For the above-mentioned indications, the appropriate dosage will of course vary depending upon, e.g., the compound employed, the host, the mode of administration and the nature and severity of the condition being treated. However, in general, satisfactory results in animals are indicated to be obtained at a daily dosage of from about 0.05 to about 150, preferably from about 0.1 mg/kg to about 100 mg/kg animal body weight. In larger mammals, e.g., humans, an indicated daily dosage is in the range from about 0.5 to about 5,000, preferably from about 1 mg to about 500 mg of a compound of formulae (I) and (Ia), conveniently administered, e.g., in divided doses up to four times a day or in sustained-release form.

The compounds of formulae (I) and (Ia) and I(B) in crystal form B, can be administered in vivo either alone or in combination with other pharmaceutical agents effective in the treatment of diseases and conditions in which vanilloid receptor activation plays a role or is implicated.

The pharmaceutical compositions can e.g. have the composition mentioned in WO 2007/065662 A2 or WO 2005/120510 A1, and can be prepared as described there.

According to another aspect the inventions provides a pharmaceutical composition comprising, as active ingredient, an effective amount of the compound of formula 1(B) in crystal form B as hereinbefore defined, optionally together with a pharmaceutically acceptable carrier.

The compound of formula 1(B) in crystal form B as hereinbefore defined can be administered in vivo either alone or in combination with other pharmaceutical agents, e.g. agents effective in the treatment of diseases and conditions in which the human VR1 activation plays a role or is implicated. A suitable combination consists of a compound of formula 1(B) in crystal form B with one or more compounds selected from the group consisting of dopamine D2 receptor antagonists, serotonin 5-HT4 receptor agonists, serotonin 5-HT3 receptor agonists, serotonin 5-HT3 receptor antagonists, CCKA receptor antagonists, motilin receptor agonists, opioid receptor antagonists, opioid receptor agonists and opiates, CRF-1 receptor antagonists, glutamate receptor antagonists, neurokinin receptor antagonists, histamine H2 receptor antagonists, histamine H4 receptor antagonists, proton pump inhibitors, chloride channel activators, guanylate cyclase-c activators, muscarinic receptor antagonists, antispasmodics, stimulant laxatives, osmotic laxatives, faecal softeners, absorbents and fibre supplements, antacids, GI relaxants, bismuth compounds, vanilloid receptor antagonists, anticonvulsants, NSAIDS, COX-2 inhibitors, GABAb receptor modulators, CB receptor ligands, calcium channel blockers, sodium channel blockers, tricyclic antidepressants, serotonin and noradrenaline re-uptake inhibitors, benzodiazepines, alpha-2 receptor agonists, and ghrelin receptor agonists.

Thus, according to a further aspect the invention provides a pharmaceutical composition comprising a compound of formula 1(B) in crystal form B as hereinbefore defined in combination with another therapeutically active ingredient, optionally in association with a pharmaceutically acceptable adjuvant, diluent or carrier.

More specifically, a compound of formula 1(B) in crystal form B may be administered as a combination with one or more compounds selected from the group consisting of dopamine D2 receptor antagonists, such as, chlorpromazine, prochlorperazine, haloperidol, alizapride, domperidone, metoclopramide and itopride; serotonin 5-HT4 receptor agonists, such as, cisapride, cinitapride, mosapride, renzapride, prucalopride, tegaserod, and compounds described in WO 2005068461 [AT-7505, Aryx], US 2005228014 and WO 2005080389, US 2006100426, US 2006100236, US 2006135764, US 2005277671, WO 2005092882, WO 2005073222, JP 2005104896, JP 2005082508, WO 2005021539, JP 2004277319, JP 2004277318, WO 2004026869, EP 1362857, WO 2006108127, US20060183901, WO 2006127815, US 20060276482, WO 2007005951, WO 2007010390 and WO 2007005951; serotonin 5-HT3 receptor agonists, such as, pumesotrag, and compounds described in WO 2007004041; serotonin 5-HT3 receptor antagonists, such as, alosetron, cilansetron, ramosetron, azasetron, ondansetron, granisetron, tropisetron, DDP225 and compounds described in WO 2006183769, WO 2006105117 and WO 2007004041; CCKA receptor antagonists, such as, devazepide, loxiglumide and dexioxiglumide; motilin receptor agonists, such as, motilin, atilmotilin, erythromycin, alemcinal, mitemcinal, KOS-2187 and compounds described in WO 2005060693 WO 2006127252 and WO 2007007018; m-opioid receptor antagonists, such as, naloxone, alvimopan and methylnaltrexone; opioid receptor agonists and opiates, such as, morphine, buprenorphine, diamorphine, dihydrocodeine, fentanyl, pethidine, asimadoline, loperamide and codeine; CRF-1 receptor antagonists, such as, GSK876008 and compounds described in WO2004069257, WO 9940089, U.S. Pat. No. 6,844,351, WO 2005013997, WO 2005014557, WO 2005023806, WO 2005026126, WO 2005028480, WO 005044793, WO 2005051954, WO 2005051954, WO 2005115399, WO 2005028480, WO 2005023806 and WO 2006044958, WO 2006044821 and US 20060211710; glutamate receptor antagonists, such as, AZD9272, AFQ056 and compounds described in WO 9902497, WO 2000020001, WO 200304758 and WO 2005030723, WO 2005077345, US 2006009443, EP 1716152, WO 2005080397, US 2006019997, WO 2005066155, WO 2005082884, WO 2005044266, WO 2005077373, EP 1713791, EP 1720860, WO 2005080379, EP 1716130, US 2006235024, WO 2005080363WO 2006114264, WO 2006114260, WO 2006089700, WO 2006114262, WO 2006123257, US 2005272779, WO 2006048771, WO 2006123249, US 2006009477, WO 2006014185, EP 1723144, US 2006025414, US 2006004021, US 2006160857, WO 2006074884, WO 2006129199, WO 2006123244, WO 2006123255, WO 2007040982, WO 2007023290, WO 2007023242, WO 2007050050, WO 2007039781, WO 2007039782 and WO 2007023245; neurokinin receptor antagonists, such as, taletant, osanetant, casopitant, nepadutrent, saredutant, DNK-333, SLV-317, SLV321, SLV317 and compounds described in EP 96-810237, WO 2006137790, WO 2006137791, WO 2006094934, WO 2007037742 and WO 2007037743; histamine H2 receptor antagonists, such as, famotidine, cimetidine, ranitidine and nizatidine; histamine H4 receptor antagonists, such as, JNJ7777120, JNJ10191584 and compounds described in US 2006111416, WO 2006050965, WO 2005092066, WO 2005054239 US 2005070550, US 2005070527, EP 1505064, WO 2007090852, WO 2007090853, WO 2007090854, US 20070232616, US 20070238771, WO 2007117399, WO 2007031529 and W02007072163; proton pump inhibitors, such as, omeprazole, lansoprazole, rabeprazole, tentoprazole, pantoprazole, esomeprazole, revaprazan soraprazan and AGN201904; chloride channel activators, such as, lubiprostone; guanylate cyclase-c activators, such as, linaclotide; muscarinic receptor antagonists, such as, darifenacin, solifenacin, atropine, dicycloverine, hycosine butyl bromide, propantheline, oxybutinin, cimetropium bromide, pinaverium bromide and otilonium bromide; antispasmodics, such as, mebeverine, tiropramide, alverine and peppermint oil; stimulant laxatives, such as, bisacodyl; osmotic laxatives, such as, activated charcoal with sorbitol, lactulose, magnesium hydroxide and phosphate buffered saline; faecal softeners, such as, senna concentrate, liquid paraffin and arachis oil; absorbents and fibre supplements, such as, bulk fibre laxatives such as bran, methylcellulose, ispaghula husk and sterculia; antacids, such as, aluminium, magnesium and calcium antacids, simeticone and alginate containing preparations; GI relaxants, such as, cholestyramine resin; bismuth compounds, such as, bismuth subsalicylate; vanilloid receptor antagonists, such as, SB-705498 and compounds described in WO 2002076946, WO 2004033435, WO 2005121116 and WO 2005120510, WO 2006006740, WO 2006006741, WO 2006010445, WO 2006016218, US 2006058308, WO 2006033620, WO 2006038871, US 2006084640, US 2006089360, WO 2006058338, WO 2006063178, US 2006128689, WO 2006062981, WO 2006065646, WO 2006068618, WO 2006068592, WO 2006068593, WO 2006076646, US 2006160872, WO 200608082, US 2006183745, WO 2006095263, WO 2006102645, WO 2006100520, US 2006241296, WO 2006122200, WO 2006120481, WO 2006122250, DE 102005044814, WO 2006122772, WO 2006122777, WO 2006124753, WO 2006122799, WO 2006122770, WO 2006122769, WO 2006136245, WO 2007030761, US 20070088072, US 20070088073, US 20070105920, WO 2007042906, WO 2007045462 and WO 2007050732; anticonvulsants, such as, carbemazepine, oxcarbemazepine, lamotrigine, gabapentin, and pregabalin; NSAIDS, such as, aspirin, acetometaphen, ibuprofen, diclofenac, naproxen, flurbiprofen, indomethacin, piroxicam, ketoprofen, sulindac and diflunisal; COX-2 inhibitors, such as, celecoxib, rofecoxib, lumiracoxib, valdecoxib, etoricoxib and compounds described in WO 2004048314; GABAb receptor modulators, such as, racemic and (R)-baclofen, AZD3355, XP19986 and compounds described in WO 2006001750 and WO 2004000856; CB receptor ligands, such as, dronabinol, nabilone, cannabidiol, rimonabant and compounds described in WO 2002042248 and WO 2003066603; calcium channel blockers, such as, ziconotide, AGI0-003, PD-217014 and compounds described in WO 2006038594, WO 2006030211 and WO 2005068448; sodium channel blockers, such as, lamotrigine and compounds described in WO 2006023757, WO 2005097136, JP 2005206590 and WO 2005047270; tricyclic antidepressants, such as, clomipramine, amoxapine, nortriptyline, amitriptyline, imipramine, desipramine, doxepin, trimipramine and protriptyline; serotonin and noradrenaline re-uptake inhibitors, such as, milnacipran, desvenlafaxine, sibutramine, duloxetine, fluoxetine, paroxetine, citalopram, sertraline and fluvoxamine; benzodiazepines, such as, levotofisopam, diazepam, lorazepam, clonazepam and alprazolam; alpha-2 receptor agonists, such as, clonidine, tizanidine and guanfacine; ghrelin receptor agonists, such as, ibutamoren, capromorelin, tabimorelin, ipamorelin, 2-Methylalanyl-N-[1(R)-formamido-2-(1H-indol-3-yl)ethyl]-D-tryptophanamide, TZP-101, TZP-102, LY-444711 and compounds described in U.S. Pat. No. 6,525,203, US 20050154043, WO 2005097788, WO2006036932, WO 2006135860, US 20060079562, WO 2006010629, WO 2006009674, WO 2006009645, US 20070021331, WO 2007020013, US 20070037857, WO 2007014258, WO 2007113202 and WO 2007118852.

BRIEF DESCRIPTION OF THE DRAWINGS

FIG. 1 illustrates the X-Ray Powder Diffraction Pattern of Polymorph B.

In the Examples which follow, which are not intended to limit, in any way, the scope of the present invention and which represent specific embodiments of the invention either as described or by generalizing the process conditions (e.g. catalysts, solvents, temperatures) as defined in the more general description above, the following abbreviations are used:

| | |
|---|---|
| AcCN | acetonitrile |
| Argonaut Reactor | Argonaut Reactor (Advantage Series ™ 4100 Process Scale-up Reactor), Biotage, Charlottesville, VA, USA |
| Celite | Celite ® (filtering aid based on diatomaceous earth, Celite Corporation, Santa Barbara, CA, USA) |
| t-BuOH | tert-butanol |
| EtOH | ethanol |
| EtOAc | ethyl acetate |
| DCM | dichloromethane |
| LOD | Limit of Detection |
| NMM | N-methylmorpholine |
| RTD | Resistance Temperature Detector |
| THF | tetrahydrofuran |
| torr | Torr (1 Torr is the static pressure caused by a mercury column of 1 mm height); 1 Torr corresponds to about 133,322 Pa |
| ~ | about |

Where subsequently the expression "collect . . . mL solvent" is used, this means that the corresponding amount of solvent is removed.

EXAMPLE 1

Preparation of 4-(7-hydroxy-2-isopropyl-4-oxo-4H-quinazolin-3-yl)-benzonitrile crystal form B

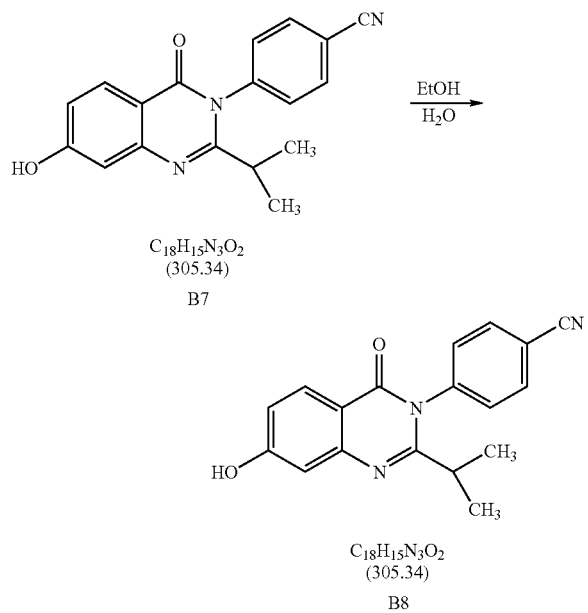

Step 1:

A seed slurry of 4-(7-hydroxy-2-isopropyl-4-oxo-4H-quinazolin-3-yl)-benzonitrile crystal form B was prepared by adding 0.0792 g (0.3% wt) of 4-(7-hydroxy-2-isopropyl-4-oxo-4H-quinazolin-3-yl)-benzonitrile form B to a glass vial. Ethanol/water (1:5 v/v) (1 mL) was added and the vial capped and the mixture was sonicated for ~1 min at 20° C. to obtain a homogeneous white slurry.

Step 2:

A vessel fitted with an agitator was charged with 4-(7-hydroxy-2-isopropyl-4-oxo-4H-quinazolin-3-yl)-benzonitrile (26.4 g), ethanol (312.5 g) and water (44.0 g). The agitator was turned on and with positive nitrogen pressure, the bulk was heated to an internal temperature of 78±3° C. (reflux) over 30 mins and then cooled to 20±3° C. over approximately 1 h. The batch temperature was maintained at a temperature of 20±3° C. for 10 min. charge quickly using a transfer pipette, 0.0792 g of Form B seed in from Step 1 in 1 ml of ethanol/water (1:5 v/v) was added to the batch and the batch held at 20±3° C. for approximately 0.5 h. The batch was cooled to 0±3° C. over approximately 0.5 h and held for approximately 0.5 h. Water (300 g) was charged into the vessel using an additional funnel over approximately 1 h, while maintaining batch temperature at 0±7° C.

The slurry was stirred at 0±3° C. for approximately 0.5 h and the suspension filtered with vacuum. The resulting cake was rinsed with a mixture of ethanol (25.3 g) and water (16.0 g). The wet cake was collected and dried at 55° C. under vacuum at 10 mbar with nitrogen purge overnight (18 h) to obtain 24.7 g of 4-(7-hydroxy-2-isopropyl-4-oxo-4H-quinazoline-3-yl)-benzonitrile (B8) as a white solid.

The isolated powder analysed by X-ray Powder Diffraction. The recorded X-ray Powder Pattern show in FIG. 1 is polymorph B. The X-ray powder pattern (XRPD) was recorded on a Bruker D8 Advance diffractometer using CuK$_\alpha$ radiation, the XRPD pattern was recorded between 2° and 40° (2-theta).

Weight of product: 24.7 g
Theoretical Yield: 26.4 g
Yield: 93.6%
Purity: 100% (by HPLC)
Polymorph Form B

TABLE 1

Powder X-Ray Diffraction Peaks for Polymorph B of 4-(7-hydroxy-2-isopropyl-4-oxo-4H-quinazolin-3-yl)-benzonitrile

| ° deg 2 θ | d-space | Relative intensity (%) |
|---|---|---|
| 9.31 | 9.491 | 28 |
| 10.60 | 8.341 | 100 |
| 12.82 | 6.898 | 13 |
| 14.41 | 6.140 | 60 |
| 15.58 | 5.683 | 35 |
| 17.90 | 4.952 | 49 |
| 19.96 | 4.446 | 35 |
| 21.31 | 4.167 | 16 |
| 23.40 | 3.799 | 55 |
| 24.21 | 3.673 | 16 |
| 24.72 | 3.598 | 18 |
| 25.37 | 3.508 | 19 |
| 28.06 | 3.178 | 59 |

Single Crystal Data of Polymorph B
Molecular formula: $C_{18}H_{15}N_3O_2$
Molecular weight (free acid): 305.34
Lattice Parameters:

| | |
|---|---|
| Space symmetry | monoclinic |
| Spacegroup | P21/n |
| Cell Volume (Å$^3$) | 1618.8 |
| Crystal Density (g/cm$^3$) | 1.254 |
| a (Å) | 8.812 |
| b (Å) | 12.279 |
| c (Å) | 15.398 |
| beta (°) | 103.976 |
| z | 4 |

EXAMPLE 2

Preparation of 4-(7-hydroxy-2-isopropyl-4-oxo-4H-quinazolin-3-yl)-benzonitrile Overview of the Synthesis:

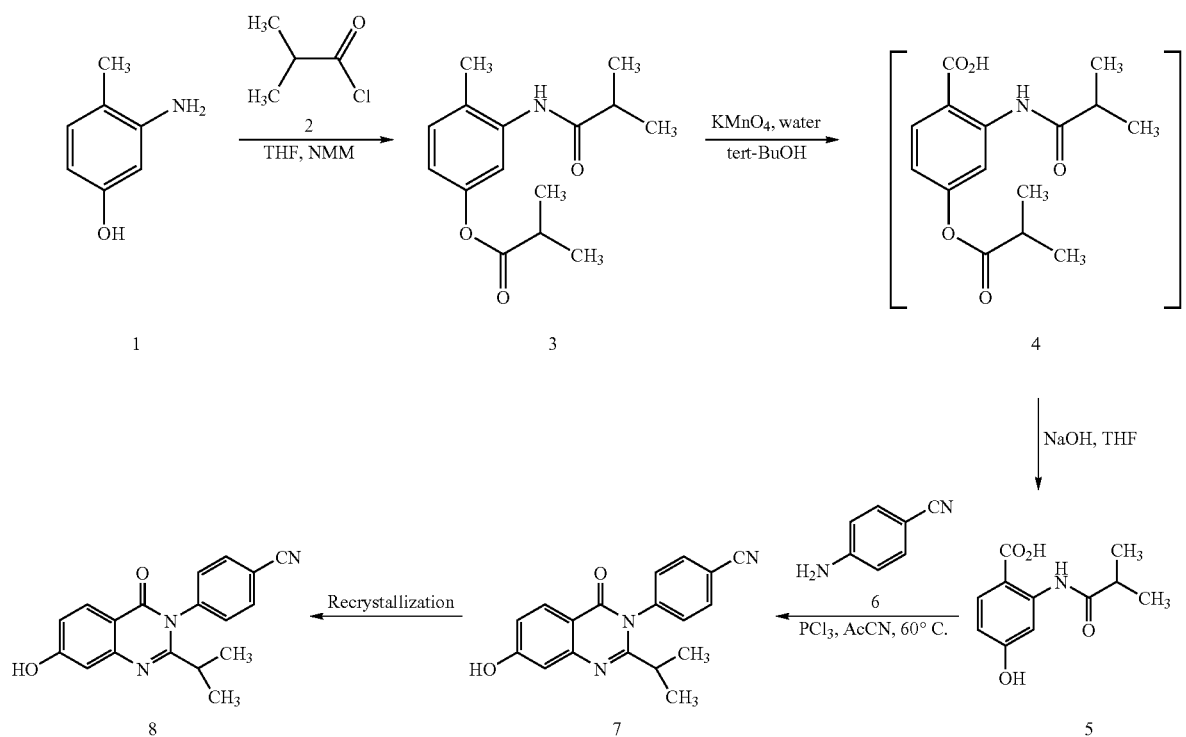

In short, the synthesis involves 3 main steps with more than 50% yield. Commercially available 3-amino-4-methylphenol 7 is used as starting material. Amide 3 is easily obtained from 1 with isobutyl chloride 2 as a simultaneous coupling and protecting agent. The novel key intermediate hydroxyl acid 5 is formed from the novel compound 3 via the novel intermediate 4 using $KMnO_4$ oxidation, followed by hydrolysis of the ester functional group in 4. The hydroxyl acid 5 is then treated with 4-aminobenzonitrile 6 in the presence of $PCl_3$ at about 60° C. The resulting crude product is then purified by recrystallisation from a mixture of EtOH and $H_2O$ to give drug substance 8 in about 75% yield.

Detailed Procedure

Step 1→3

A 2-L Argonaut reactor, equipped with a mechanical stirrer, nitrogen inlet-outlet, digital thermometer and heating jacket, was charged with 100 g of 3-amino-4-methylphenol (1) (AK Scientific, Inc., Mountain View, Calif., USA), 700 mL of THF and 188.9 g (2.3 equiv, 204.8 mL) of NMM. The solution was stirred at −15±5° C. for 10 min and 199.0 g (2.3 equiv, 197.2 mL) of isobutyryl chloride (2) (Sigma-Aldrich, Inc., St. Louis, Mo., USA) were added over a period of 2 hours while maintaining an internal temperature of −15±5° C. The mixture was stirred at −15±5° C. for 1 h and then 200 g of water were added over a period of 20 min while maintaining an internal temperature of −10±5° C. The resulting solution was stirred at −10±5° C. for 20 min. The solvent was concentrated under vacuum (100-50 torr) at an internal temperature of 20-30° C. to collect about 700 mL of solvent (batch volume ~700 mL). Then 400 mL of toluene were added. The organic layer was collected and washed with 80 mL of 0.5 N NaOH (0.05 equiv) solution, (optional, only if the reaction was not completed and some monomer (N-acylated compound) generated was found by HPLC>0.3%) and 100 mL of water. The solvent was concentrated under vacuum (100-40 torr) at an internal temperature of 25-35° C. to collect ≈250 mL of solvent (batch volume ≈450 mL), and 850 mL of heptanes was slowly added over a period of one hour while rapidly stirring and maintaining an internal temperature of 37±3° C. Then the solution was slowly cooled down to 15° C. over a period of 1 hour while rapidly stirring. The solid was collected by filtration over a Büchner funnel, and the filter cake was washed with 200 mL of heptanes. The resulting solid was dried under vacuum (100-50 torr) at 35-40° C. with nitrogen bleeding until LOD<1% (8 h) to obtain 191.0 g of 3 as a slightly yellow solid.

$^1$H NMR (400 MHz, $CDCl_3$): δ 7.78 (s, 1H), 7.16 (d, 1H), 7.01 (s, 1H), 6.78 (d, 1H), 2.77 (m, 1H), 2.55 (m, 1H), 1.30 (d, 6H), 1.26 (d, 6H); ESI-MS: m/z: 264.1 [M+H]$^+$

Step 3→[4]→5

A 2-L Argonaut reactor, equipped with mechanical stirrer, addition funnel, and nitrogen inlet/outlet, was charged with 180.6 g (4.0 equiv) of $KMnO_4$ and 525 g of $H_2O$. The mixture was stirred at 20±3° C. for 30 min. A solution of 75 g (285.2 mmol) of isobutyric acid 3-isobutyrylamino-4-methyl-phenyl ester (3) was added in 293 g of t-BuOH over a period of 1 h while maintaining the internal temperature at 25±3° C. The suspension was stirred at 25±3° C. for 6 h and at 20±3° C. for 16 h. 1 ml samples for process steering control were taken.

400 g of 30(Wt) % $NaHSO_3$ solution were added while maintaining the internal temperature at 20±10° C. The mixture was stirred at 20±10° C. for 60 min. 328 g of isopropyl acetate were added. The resulting solution was collected by filtration over a Celite pad in a Büchner funnel with suction and the filter cake was washed with 66 g of isopropyl acetate and 75 g of water. Addition of 75 g of 6 N HCl solution to the filtrate followed while maintaining the internal temperature at 20±10° C. The mixture was stirred for 10 min, and the organic layer was separated off. 375 g of water were added to the organic layer, and the resulting mixture was stirred for 15 min. The organic layer was separated off. The solvent was concentrated under vacuum (100-50 torr) at an internal temperature of 25±5° C. to collect ~450 mL of solvent (batch volume ~150 mL). 176 g of THF were then added to the residue. The solvent was again concentrated under vacuum (100-50 torr) at an internal temperature of 25±5° C. to collect ~200 mL of solvent (batch volume ~150 mL). Again 176 g of THF were added. The solvent was concentrated under vacuum (100-50 torr) at an internal temperature of 25±5° C. to collect ~200 mL of solvent (batch volume ~150 mL) to obtain 150 g of THF solution of crude 2-isobutyrylamino-4-isobutyryloxy-benzoic acid 4 (containing ~75 g 4).

$^1$H NMR (500 MHz, CDCl$_3$):

δ 11.04 (s, 1H), 8.58 (d, 1H, J=5.0 Hz), 8.14 (d, 1H, J=10.0 Hz,), 6.87 (dd, 1H, J=10.0, 5.0 Hz), 2.80 (m, 1H), 2.62 (m, 1H), 1.31 (d, 6H, J=5.0 Hz), 1.28 (d, 6H, J=5.0 Hz).

ESI-MS: m/z 294.0 [M+H]$^+$

To this solution, 330 g of THF and 285 g of 3N NaOH (3 equiv) solution were added. The mixture was stirred at 20±3° C. for 2 h. Samples for process steering control were taken. The solvent was concentrated under vacuum (100-50 torr) at an internal temperature of 25±5° C. to collect ~375 mL of solvent (batch volume ~300 mL). To the remaining solution, 100 g of H$_2$O and 315 g of 3N HCl solution were added while maintaining the internal temperature at 20±10° C. Stirring for an additional 30 min followed. The solid was collected by filtration over a polypropylene filter paper in a Büchner funnel with suction. The filter cake was washed with 2×50 g of H$_2$O. The solid was dried under vacuum (100-150 mbar) at 40-45° C. with nitrogen bleeding until <1% LOD (24 h) to obtain 47.7 g of 4-hydroxy-2-isobutyrylamino-benzoic acid (5) as a white solid.

$^1$H NMR (500 MHz, DMSO-d$^6$):

δ 13.04 (s, 1H), 10.38 (s, 1H), 8.13 (s, 1H), 7.86 (d, 1H, J=10.0 Hz), 6.52 (d, 1H, J=10.0 Hz), 2.55 (m, 1H), 1.18 (d, 6H, J=7.5 Hz).

ESI-MS: m/z 224.0 [M+H]$^+$

Step 5+6→8

A 2-L Argonaut reactor, equipped with pitched-blade impeller, RTD sensor, reflux condenser, addition funnel, and nitrogen inlet-outlet, was charged with 54.90 g (246.0 mmol) of 4-hydroxy-2-isobutyrylamino-benzoic acid (5), 31.96 g (270.6 mmol) of 4-aminobenzonitrile (6) and 919.2 g (1.177 L) of AcCN. The suspension was stirred at 22±3° C. for 30 min with an efficient mixing, and 70.97 g (45.09 mL, 516.7 mmol) of PCl$_3$ were added while maintaining an internal temperature of 22±10° C. The suspension was then warmed to an internal temperature of 60±3° C. over 1 h, and the mixture was stirred at 60±3° C. for 20 h with an efficient mixing. The suspension was cooled to an internal temperature of 15±3° C. over 30 min, and then 54.275 g (1356.87 mmol) of NaOH in 220 g of water were added while maintaining an internal temperature of 15±10° C. The suspension was warmed to an internal temperature of 75±5° C. over 1 h, then the mixture was stirred at this temperature for 30 min. Then the mixture was cooled to an internal temperature of 30±5° C. over 45 min, and the organic layer was separated off. The organic layer was then line-filtered by pressure (300 to 500 mbar) and the solvent was concentrated under vacuum (100-50 torr) at an internal temperature of 20-30° C. to collect ~950 mL of solvent (batch volume ~200 mL). 875 mL of water were added to the concentrate. Again the solvent was concentrated under vacuum (200-150 torr) at an internal temperature of 20-30° C. to collect ~200 mL of solvent (batch volume ~820 mL). The remaining suspension was stirred at 20±3° C. for 2 h, and the solid was removed by filtration over a polypropylene filter paper in a Büchner funnel with suction. The filter cake was washed with 2×100 mL of H$_2$O. The solid was dried under vacuum (100-150 mbar) at 50±5° C. with nitrogen bleeding until ≦1% LOD (15 h) to obtain 56.5 g of 4-(7-hydroxy-2-isopropyl-4-oxo-4H-quinazoline-3-yl)-benzonitrile (7) as a white solid.

A 2-L Argonaut reactor, equipped with pitched-blade impeller, RTD sensor, reflux condenser, addition funnel, and nitrogen inlet-outlet, was charged with 50.0 g of 4-(7-hydroxy-2-isopropyl-4-oxo-4H-quinazoline-3-yl)-benzonitrile (7) and 750.0 mL of EtOH. The suspension was heated to an internal temperature of 78±3° C. over 30 min (or until a clear solution was obtained). The solution was cooled to an internal temperature of 65±5° C. over 20 min, and the solution was line-filtered by pressure (300 to 500 mbar). The solvent was concentrated under vacuum (100-50 torr) at an internal temperature of 20-30° C. to collect ~280 mL of solvent (batch volume ~450 mL). The remaining suspension was heated to an internal temperature of 78±3° C. over 30 min. 50 mL of H$_2$O were added to it over a period of 30 min while maintaining an internal temperature of 78±5° C. The mixture was then cooled to an internal temperature of 20±3° C. over 1 h. Then 175 mL of H$_2$O were added over a period of 30 min while maintaining an internal temperature of 20±5° C. The resulting suspension was stirred at 20±3° C. for 8 h, and the solid was collected by filtration over a polypropylene filter paper in a Büchner funnel with suction. The filter cake was washed with 2×100 mL of a mixture of ethanol and H$_2$O (2:1 v/v). Then the solid was dried under vacuum (100-150 mbar) at 50±5° C. with nitrogen bleeding until <1% LOD (12 h) to obtain the final pure product, 40.0 g of 4-(7-hydroxy-2-isopropyl-4-oxo-4H-quinazoline-3-yl)-benzonitrile (8), which was obtained as a white solid. The crude 4-(7-hydroxy-2-isopropyl-4-oxo-4H-quinazoline-3-yl)-benzonitrile (8) was recrystallised from EtOH/H$_2$O (1:5) to afford polymorph B as desired form. Yield 76% and 100% purity.

$^1$H NMR (400 MHz, CD$_3$OD): δ=8.10-7.95 (m, 3H), 7.7.67-7.60 (m, 2H), 7.13-6.95 (m, 2H), 3.35 (s, 1H), 2.67-2.52 (m, 1H), 1.26 (d, 6H, J=7.0 Hz); ESI-MS: m/z: 306.4 [M+H]$^+$

EXAMPLE 3

3-(4-chlorophenyl)-7-hydroxy-2-Isopropyl-3H-quinazolin-4-one

The compound is prepared according to the processes and methods described herein.

EXAMPLES 4 TO 44

The compounds in the following table are prepared according to the processes and methods described herein:

| Example | Structure |
|---|---|
| 4 | (structure shown) |

-continued
| Example | Structure |
|---|---|
| 5 | 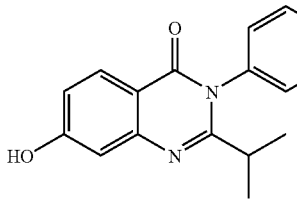 |
| 6 | 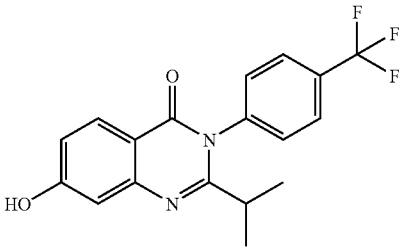 [SMILES: CC(C)c1nc2cc(O)ccc2c(=O)n1-c1ccc(C(F)(F)F)cc1] |
| 7 | 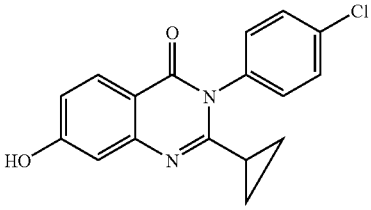 [SMILES: O=c1c2ccc(O)cc2nc(C2CC2)n1-c1ccc(Cl)cc1] |
| 8 | 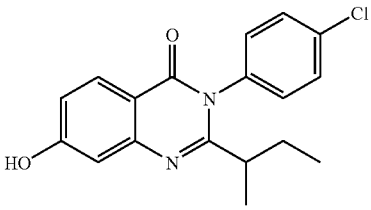 [SMILES: CCC(C)c1nc2cc(O)ccc2c(=O)n1-c1ccc(Cl)cc1] |
| 9 | 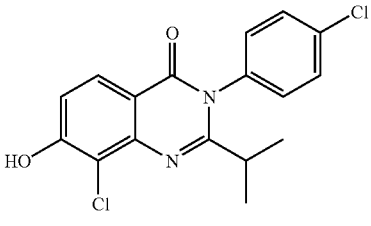 |
| 10 | 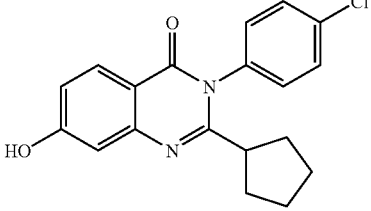 |
| 11 | 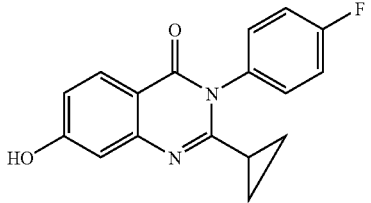 [SMILES: O=c1c2ccc(O)cc2nc(C2CC2)n1-c1ccc(F)cc1] |
-continued
| Example | Structure |
|---|---|
| 12 | 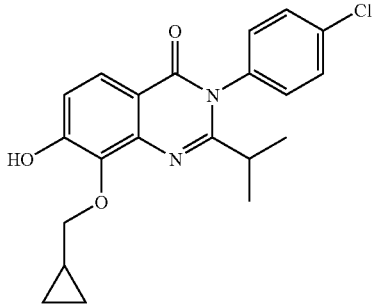 [SMILES: CC(C)c1nc2c(OCC3CC3)c(O)ccc2c(=O)n1-c1ccc(Cl)cc1] |
| 13 | 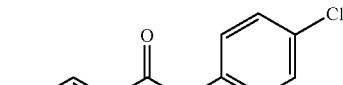 |
| 14 | 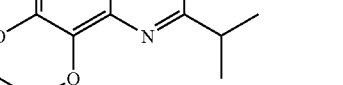 |
| 15 | 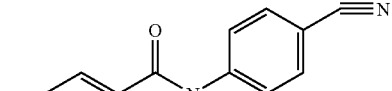 |
| 16 | 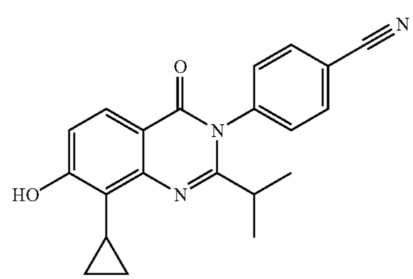 [SMILES: CC(C)c1nc2c(C3CC3)c(O)ccc2c(=O)n1-c1ccc(C#N)cc1] |

| Example | Structure |
|---|---|
| 17 | 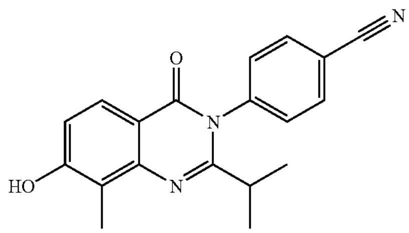 [SMILES: Cc1c(O)ccc2c(=O)n(-c3ccc(C#N)cc3)c(C(C)C)nc12] |
| 18 | 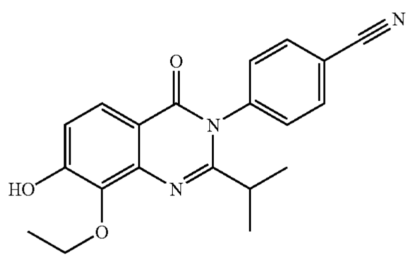 [SMILES: CCOc1c(O)ccc2c(=O)n(-c3ccc(C#N)cc3)c(C(C)C)nc12] |
| 19 | 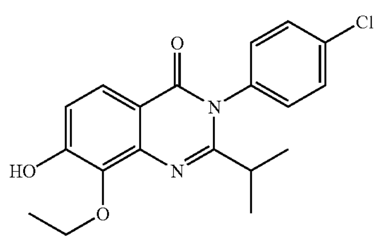 [SMILES: CCOc1c(O)ccc2c(=O)n(-c3ccc(Cl)cc3)c(C(C)C)nc12] |
| 20 | 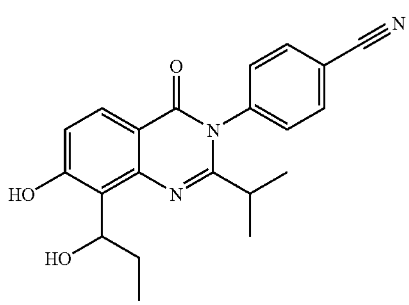 [SMILES: CCC(O)c1c(O)ccc2c(=O)n(-c3ccc(C#N)cc3)c(C(C)C)nc12] |
| 21 | 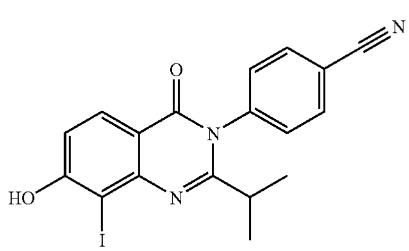 [SMILES: CC(C)c1nc2c(I)c(O)ccc2c(=O)n1-c1ccc(C#N)cc1] |
| 22 | 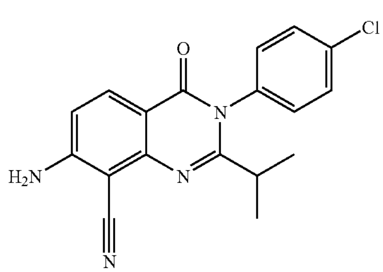 [SMILES: CC(C)c1nc2c(C#N)c(N)ccc2c(=O)n1-c1ccc(Cl)cc1] |
| 23 | |
| 24 | |
| 25 | |
| 26 | |
| 27 | |

| Example | Structure |
|---|---|
| 28 | 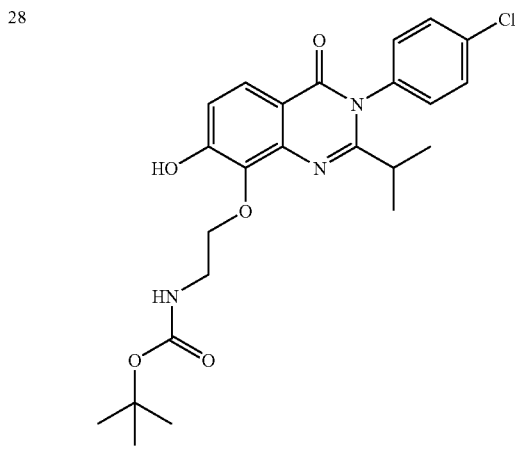 |
| 29 | 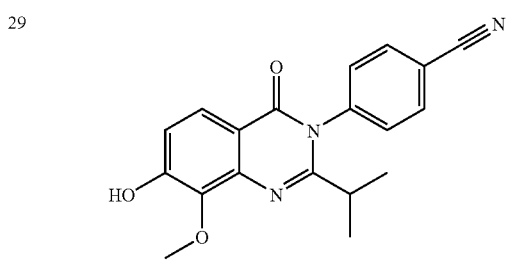 |
| 30 | 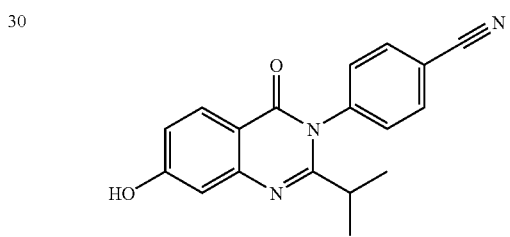 |
| 31 | 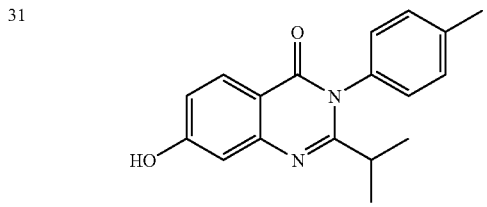 |
| 32 | 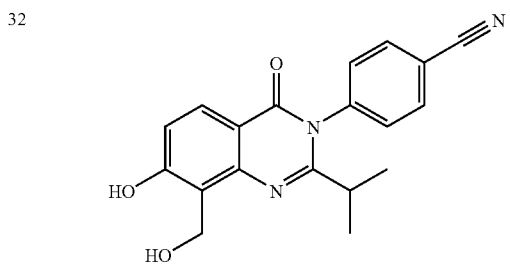 |
| Example | Structure |
|---|---|
| 33 | 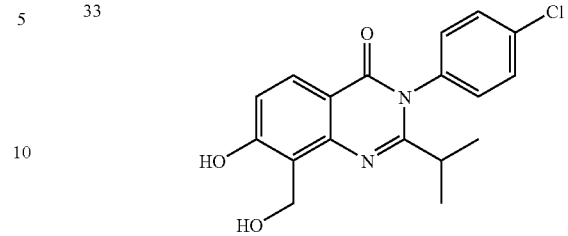 |
| 34 | 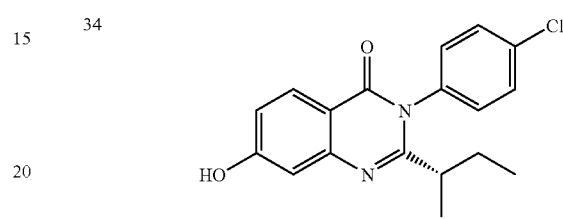 |
| 35 | 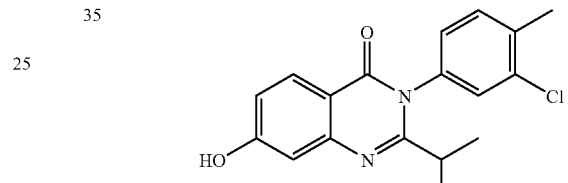 |
| 36 | 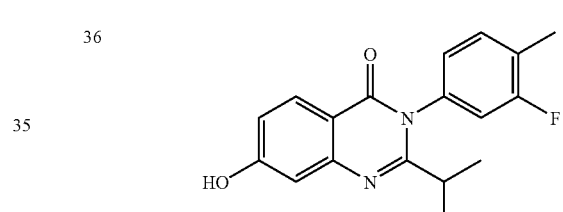 |
| 37 | 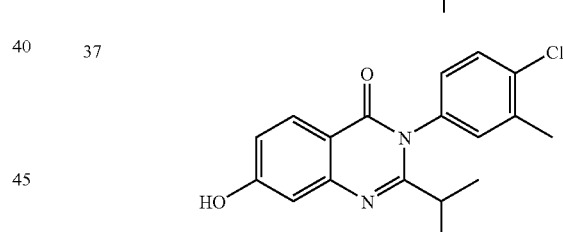 |
| 38 | 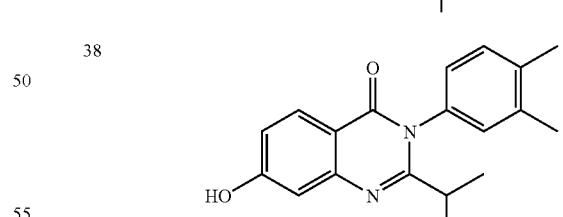 |
| 39 | 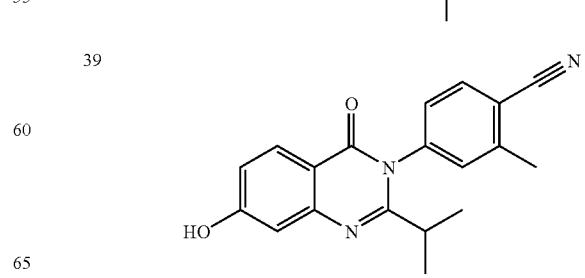 |

| Example | Structure |
|---|---|
| 40 | (4-chlorophenyl)-substituted quinazolinone with 7-HO, 8-O-CH₂CH₂NHC(O)C(CH₃)₃, 2-isopropyl |
| 41 | 3-(4-chloro-3-fluorophenyl)-7-hydroxy-8-formyl-2-isopropyl-quinazolin-4(3H)-one |
| 42 | 3-(6-chloropyridin-3-yl)-7-hydroxy-2-isopropyl-quinazolin-4(3H)-one |
| 43 | 3-(6-cyanopyridin-3-yl)-7-hydroxy-2-isopropyl-quinazolin-4(3H)-one |
| 44 | 3-(3-cyano-4-fluorophenyl)-7-hydroxy-2-isopropyl-quinazolin-4(3H)-one |

The invention claimed is:

1. The crystal form B of 4-(7-hydroxy-2-isopropyl-4-oxo-4H-quinazolin-3-yl)-benzonitrile having structural formula I(B);

I(B)

characterized by an X-ray diffraction pattern having three or more peaks at 2θ values selected from 9.3, 10.6 and 14.4±0.2°2θ.

2. A method of preparing a compound of formula I(B) in crystal form B according to claim 1 which comprises crystallising the compound of formula I(B) from a solution thereof in water and a water miscible organic solvent.

3. A pharmaceutical composition comprising, as active ingredient, an effective amount of the compound of formula 1(B) in crystal form B according to claim 1, optionally together with a pharmaceutically acceptable carrier.

4. The crystal form B of 4-(7-hydroxy-2-isopropyl-4-oxo-4H-quinazolin-3-yl)-benzonitrile having structural formula I(B) according to claim 1 characterized by an X-ray diffraction pattern having three or more peaks at 2θ values selected from 9.3, 10.6, 14.4, 15.5, 17.9, 19.9, 23.4±0.2°2θ.

5. A pharmaceutical composition comprising, as active ingredient, an effective amount of the compound of formula 1(B) in crystal form B according to claim 4, optionally together with a pharmaceutically acceptable carrier.

* * * * *